United States Patent
Stevenson et al.

(10) Patent No.: US 10,184,073 B2
(45) Date of Patent: Jan. 22, 2019

(54) EMULSION INCLUDING POLYMERS CONTAINING A 1,1-DISUBSTITUTED ALKENE COMPOUND, ADHESIVES, COATINGS, AND METHODS THEREOF

(71) Applicant: Sirrus, Inc., Loveland, OH (US)

(72) Inventors: Peter Rulon Stevenson, Salt Lake City, UT (US); Alexander R. Holzer, Cincinnati, OH (US); Aniruddha Sudhir Palsule, Cincinnati, OH (US); Jeffrey M. Sullivan, Goshen, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/467,597

(22) Filed: Mar. 23, 2017

(65) Prior Publication Data

US 2017/0198181 A1    Jul. 13, 2017

Related U.S. Application Data

(63) Continuation of application No. 14/966,409, filed on Dec. 11, 2015, now Pat. No. 9,637,564, which is a
(Continued)

(51) Int. Cl.
*C09J 135/02* (2006.01)
*C09D 7/65* (2018.01)
(Continued)

(52) U.S. Cl.
CPC ............. *C09J 135/02* (2013.01); *B01J 19/10* (2013.01); *B01J 19/18* (2013.01); *C08F 2/26* (2013.01);
(Continued)

(58) Field of Classification Search
None
See application file for complete search history.

(56) References Cited

U.S. PATENT DOCUMENTS 2,212,506 A    8/1940    Gustave et al.
2,245,567 A    6/1941    Brant et al.
(Continued)

FOREIGN PATENT DOCUMENTS

CN    102901754 A    1/2013
DE    19508049 A1    9/1996
(Continued)

OTHER PUBLICATIONS

"Adhesives in Transdermal Drug Delivery Systems: Sticking it to Them Since 1979" by Leslie Townsend Ferguson, published on www.frost.com on Oct. 31, 2005.*
(Continued)

*Primary Examiner* — Vu A Nguyen
(74) *Attorney, Agent, or Firm* — Young Basile Hanlon & MacFarlane, P.C.

(57) ABSTRACT

The present teachings show that it is possible to polymerize 1,1-disubstituted alkene compounds in an emulsion (for example using a water based carrier liquid), despite the possible reactions between the monomer and water. Polymerization of 1,1-disubstituted alkene compounds in an emulsion provides opportunities to better control the polymerization compared with bulk polymerization. The emulsion polymerization techniques can be employed for preparing homopolymers, copolymers (e.g., random copolymers), and block copolymers.

20 Claims, 3 Drawing Sheets

Related U.S. Application Data continuation of application No. 14/789,178, filed on Jul. 1, 2015, now Pat. No. 9,249,265.

(60) Provisional application No. 62/186,479, filed on Jun. 30, 2015, provisional application No. 62/182,076, filed on Jun. 19, 2015, provisional application No. 62/047,283, filed on Sep. 8, 2014, provisional application No. 62/047,328, filed on Sep. 8, 2014.

(51) Int. Cl.

| | | |
|---|---|---|
| C08F 2/26 | (2006.01) | |
| C08F 22/14 | (2006.01) | |
| C08F 122/14 | (2006.01) | |
| C08J 3/07 | (2006.01) | |
| C08F 22/10 | (2006.01) | |
| B01J 19/10 | (2006.01) | |
| B01J 19/18 | (2006.01) | |
| C08F 2/30 | (2006.01) | |
| C08F 267/06 | (2006.01) | |
| C09D 7/63 | (2018.01) | |
| C09D 135/02 | (2006.01) | |
| C09J 11/06 | (2006.01) | |
| C09J 11/08 | (2006.01) | |
| C08K 5/103 | (2006.01) | |
| C08K 5/1535 | (2006.01) | |
| C08K 5/42 | (2006.01) | |

(52) U.S. Cl.
CPC ............... *C08F 2/30* (2013.01); *C08F 22/10* (2013.01); *C08F 122/14* (2013.01); *C08F 267/06* (2013.01); *C08J 3/07* (2013.01); *C09D 7/63* (2018.01); *C09D 7/65* (2018.01); *C09D 135/02* (2013.01); *C09J 11/06* (2013.01); *C09J 11/08* (2013.01); *C08K 5/103* (2013.01); *C08K 5/1535* (2013.01); *C08K 5/42* (2013.01)

(56) References Cited

U.S. PATENT DOCUMENTS

| | | |
|---|---|---|
| 2,403,791 A | 7/1941 | D'Aiello |
| 2,277,479 A | 3/1942 | D'Aiello |
| 2,313,501 A | 3/1943 | Gustave |
| 2,330,033 A | 9/1943 | D'Aiello |
| 3,042,710 A | 7/1962 | Dickstein et al. |
| 3,197,318 A | 7/1965 | Kitazawa et al. |
| 3,203,915 A | 8/1965 | D'Aiello |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,246,203 A | 9/1993 | McKnight et al. |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |

(56) References Cited

U.S. PATENT DOCUMENTS

| | | |
|---|---|---|
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 * | 7/2002 | Bru-Magniez ....... A61K 9/5138 524/365 |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B1 | 11/2010 | Brammer et al. |
| 7,900,558 B2 | 3/2011 | Yokoi |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,481,640 B2 | 11/2016 | McArdle et al. |
| 2001/0005572 A1 | 6/2001 | Lobo et al. |
| 2001/0034300 A1 | 10/2001 | Yurugu et al. |
| 2002/0035231 A1 | 3/2002 | Whitehouse et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2004/0082043 A1 | 4/2004 | Yadav et al. |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 10/2007 | Malofsky et al. |
| 2007/0238872 A1 | 10/2007 | Sabesan |
| 2008/0131618 A1 | 6/2008 | Nakamura et al. |
| 2008/0138418 A1 | 6/2008 | Lee et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0206861 A1 | 8/2009 | Shiraishi et al. |
| 2009/0263604 A1 | 10/2009 | Arai et al. |
| 2010/0016508 A1 | 1/2010 | Sasagawa et al. |
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2012/0083523 A1 | 4/2012 | Richard et al. |
| 2012/0136130 A1 | 5/2012 | Takashima et al. |
| 2012/0203021 A1 | 8/2012 | Friese et al. |
| 2013/0019520 A1 | 1/2013 | Sello et al. |
| 2013/0281580 A1 | 10/2013 | Malofsky et al. |
| 2013/0303719 A1 | 11/2013 | Malofsky et al. |
| 2013/0324754 A1 | 12/2013 | Bredsguard |
| 2014/0058031 A1 | 2/2014 | Overbeek et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |
| 2016/0068616 A1 | 3/2016 | Palsule et al. |
| 2016/0096906 A1 | 4/2016 | Palsule et al. |

FOREIGN PATENT DOCUMENTS

| | | |
|---|---|---|
| EP | 2768917 A2 | 2/2009 |
| FR | 2788516 A1 | 7/2000 |
| GB | 432628 A | 7/1935 |
| GB | 965676 | 8/1964 |
| GB | 965767 | 8/1964 |
| GB | 975733 | 11/1964 |
| JP | S56-081537 A | 7/1981 |
| JP | H02-281013 A | 11/1990 |
| JP | H08231564 | 9/1996 |
| JP | 09258448 A | 10/1997 |
| JP | 200019936 | 7/2000 |
| JP | 2003201397 A | 7/2003 |
| JP | 2008/174494 | 1/2007 |
| WO | 1999/046619 | 9/1999 |
| WO | 99/055394 A1 | 11/1999 |
| WO | 2007/120630 A2 | 10/2007 |
| WO | 2010/091975 A1 | 8/2010 |
| WO | 2010/129068 A1 | 11/2010 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013/059473 | 4/2013 |
| WO | 2013/066629 | 5/2013 |
| WO | 2013/149165 A1 | 10/2013 |

(56) References Cited

FOREIGN PATENT DOCUMENTS

| | | |
|---|---|---|
| WO | 2013/149168 A1 | 10/2013 |
| WO | 2013/149173 A1 | 10/2013 |

OTHER PUBLICATIONS

Lecture Notes by Professor A. Kraft of Heriot Watt University (Scotland) published online at http://www.che.hw.ac.uk/teaching/B11MS1/Material/Synthesis/AnionicPolymerization.htm.*
"Comparison of the catalytic activity of MOFs and zeolites in Knoevenagel condensation", Maksym Opanasenko, et al., Catalysis Science & Technology, vol. 3 p. 500-507. (2013).
"Knoevenagel Condensation Over Acidic Zeolite", Zuo Bojun et al., Chinese Journal ofCatalysis, vol. 23 (6), pp. 555-558. (2002).
"Knoevenagel reaction on a molecular sieve", Li Qifang et al., Chinese Science Bulletin, vol. 12, pp. 914-917. (1988).
"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.
Bachman et al., "Diethyl Methylenemalonate" Contirbution from the Research Laboratories of the Eastman Kodak Company, May 17, 1939, pp. 493-501.
Corey et al. "Total Synthesis of Gibberellic Acid. A Simple Synthesiss of a Key Intermediate", J. Am. Chem. Soc. 1982, 104, 6129-6130.
Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.
K. Okamura and T. Date, A Facile Conversion of Ethoxydihydropyrans to 4-Cyanoethylisoxazoles, J. Heterocyclic Chem. 33, 383 (1996).
Krishna et al. "Stereodefined Access to 3-Deoxy Sugars Through a Tandem Baylis-Hillman and Lewis Acid Catalyzed Sequence", European Journal of Organic Chemistry, 2010, 813-817.
Kütt et al., "Equilibrium Acidities of Superacids," Journal of Organic Chemistry, vol. 76, No. 2, 2011, pp. 391-95, published on the web Dec. 17, 2010.
M. Matziari et al. Active Methylene Phosphinic Peptides: A new Diversification Approach Organic Letters 2006 vol. 8, No. 11 pp. 2317-2319 May 5, 2006.
March, *Advanced Organic Chemistry*, 2d Ed, section 0-25, pp. 365-367, 1977, McGraw Hill, New York, New York.
Morrison and Boyd, *Organic Chemistry*, $4^{th}$ Ed., pp. 831 and 836-838, 1983, Allyn Bacon, Inc., Boston, MA.
Olah et al., "Superelectrophilic Solvation," Accounts of Chemical Research, Apr. 2004, vol. 37, No. 4.
Otera et al., "Esterification: Methods, Reactions, and Applications", $2^{nd}$ Ed., pp. 55-58, 2010, Wiley-VCH Verlag Gmbh & Co. KGaA. Weinheim, Germany.
Transsesterification of diethyl malonate with Benzyl Alcohol Catalyzed by Modified Zirconia: Kinetic Study, Journal of Molecular Catalysis A: Chemical, vol. 391, Sep. 2014, pp. 55-65.
Yamauchi et al. *Reactivity of 2-Methylene-1,3-Dicarbonyl Compounds: Catalytic Enantioselective Diels-Alder Reaction* dated 2001, pp. 3113-3118.
Yamauchi et al. *A Facile Conversion of Ethoxydihydropyrans to 4-Cyanoethylisoxazoles*, Mar.-Apr. 1996, pp. 383-387.
Zaragoza Dorwald, Side Reactions in Organic Synthesis, 2005, Wiley-VCH Verlag GmbH & Co., KgaA, Weinheim, Preface. p. IX.
Christoph Schotes et al. "Cu(I)- and C(II)-Catalyzed Cyclo- and Michael Addition Reactions of Unsaturated [beta]-Ketoesters" The Journal of Organic Chemistry, vol. 76, No. 14 dated Jul. 15, 2011 p. 5862-5866.
Alejandro Bugarin et al. "Efficient direct [alpha]-methylenation of carbonyls mediated by dissopropylammonium trifluoroacetate", Chemical Communications, vol. 46, No. 10 dated Jan. 25, 2010.
H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jan. 1, 2001, pp. 1638-1639.
Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.
Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2., compound 3*.
P. Breton et al., "New Poly(Methylidudene Malonate 2.1.2) Nanoparticles: Recent Developments", Targeting of Drugs 4, NATO ASI Series, vol. 273, pp. 161-172, 1994.
Limouzin et al., "Anionic Polymerization of n-Butyl Cyanoacrylate in Emulsion and Miniemulsion" Macromolecules, vol. 36, 2003, pp. 667-674.
Copending U.S. Appl. No. 14/810,741, filed Jul. 28, 2015.
Copending PCT Patent Application No. PCT/US2015/048846 filed on Sep. 8, 2015.
International Search Report and Written Opinion, Appliction No. PCT/US15/47466 dated Dec. 1, 2015.
International Search Report and Written Opinion, Appliction No. PCT/US15/47445 dated Nov. 30, 2015.
McCoy, M. "A New Way to Stick" Chemical & Engineering News, vol. 92, Issue 26, Jun. 30, 2014, pp. 17-18, paragraph [2].
International Search Report and Written Opinion for PCT Application No. PCT/US2011/56926 dated Feb. 28, 2012.
Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
McNab, Kirk-Othmer Encyclopedia of chemical Technology, Pyrolysis, Flash Vacuum, 2009, John Wiley & Sons, Inc., pp. 1-26.
Block, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.
Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.
M. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.
J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.
B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.
H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.
H. Jiang et al.: "Inorganic Zinc Salts Catalyzed Knoevenagel Condensation at Room Temperature without Solvent," Preparative Biochemistry & Biotechnology, (2009), vol. 39, pp. 194-200.
T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.
H. Jung et al,: "New and General Methods for the Synthesis of Arylmethylene Bis(3-Hydroxy-2-Cyclohexene-1-Ones) and Xanthenediones by EDDA and ln(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

(56) References Cited

OTHER PUBLICATIONS

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,—(1998), vol. 39, No. I, pp. 173-181.

C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a.

P, Ballesteros et al.: "D I-tert-Butyl Methylenemalonate [Propanedioic Acid, Methylene-, bis( 1,1-dimethylethyl)esterl," Or!=)anic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No, 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.

P. Ballesteros et al.: "Synthesis of Dl-tent-Butyl Methylenemalonate, a Sterically Hindered 1,1-Dicarbonyl Alkene," J. Ora <htto://J. Ora>. Chem, (1983), vol. 48, pp. 3603-3605.

European Extended Search Report for Application No. PCT/2011056926 dated May 27, 2015.

Magdalini Matziari et al: "Active methylene phosphinic peptides: a new diversification approach", Organic Letters., vol. 8, No. 11, 2006, pp. 2317-2319, USACS, Washington, DC. ISSN: 1523-7060.

Australian Patent Examination Report No. 1, Application No. 2011317050, dated Jan. 9, 2015.

Larras et al. Synthesis and micellization of amphiphilic poly(ethylene oxide)-block-poly(methylidene malonate 2.1.2.) diblock copolymers Macromol. Rapid Commun. dated2000, vol. 21, pp. 1089-1029.

Copending U.S. Appl. No. 14/810,740, filed Jul. 28, 2015 published as US2016/0068616 dated Mar. 10, 2016.

Copending U.S. Appl. No. 14/966,247, filed Dec. 11, 2015, published as US2016/0096906 dated Apr. 7, 2016.

Copending U.S. Appl. No. 15/509,403, filed Mar. 7, 2017.

Copending U.S. Appl. No. 15/467,330 filed Mar. 23, 2017.

* cited by examiner

EMULSION INCLUDING POLYMERS CONTAINING A 1,1-DISUBSTITUTED ALKENE COMPOUND, ADHESIVES, COATINGS, AND METHODS THEREOF

CLAIM OF PRIORITY

The present application is a continuation of U.S. patent application Ser. No. 14/966,409 filed on Dec. 11, 2015, the contents of which are incorporated herein by reference in its entirety. The present application also claims priority to U.S. patent application Ser. No. 14/789,178 filed on Jul. 1, 2015, and U.S. Provisional Patent Applications Nos. 62/186,479 filed on Jun. 30, 2015, 62/182,076 filed on Jun. 19, 2015, 62/047,283 filed on Sep. 8, 2014, and 62/047,328 filed on Sep. 8, 2014, all incorporated herein by reference in their entirety.

FIELD

The teachings herein are directed at emulsion polymers including one or more 1,1-disubstituted alkene compounds having a hydrocarbyl group bonded to the carbonyl groups through a direct bond or through an oxygen atom, methods for preparing the emulsion polymers, compositions including the emulsion polymers, and the use of the emulsion polymers. The emulsion polymers may be homopolymers consisting essentially of (e.g., about 99 weight percent or more) or entirely of a single monomer or may be copolymers including two or more monomers (e.g., a random copolymer or a block copolymer having a plurality of polymer blocks). The emulsion polymerization preferably is prepared by anionic polymerization of one or more reactive 1,1-disubstituted alkene monomers.

BACKGROUND

Polymerization of 1,1-disubstituted alkene compounds are typically performed in bulk state, and frequently in situ, such as when monomer is placed between two substrates to be adhered. The resulting polymerization process may be difficult to control resulting in variable performance or mechanical properties. For example, the polymerization process may be characterized by one or more spikes in temperature during the polymerization process, such as by an increase in temperature of about 15° C. or more, about 30° C. or more, or even about 45° C. or more (e.g., during a polymerization reaction). Such an increase in temperature may occur in a short time period (e.g., less than 10 minutes, less than 3 minutes, or even less than 1 minute). Typically, the resulting polymer may be characterized by one or more of the following: a generally high level of branching, a high polydispersity index, a high concentration of non-polymer reaction products, a generally high viscosity, or a generally high molecular weight. For example, when polymerized in bulk, the resulting polymer may have a high viscosity that makes further processing and/or handling difficult.

As used herein, bulk polymerization refers to the polymerization of a polymerizable composition including one or more monomers where the concentration of the one or more monomers is about 80 weight percent or more, preferably about 90 weight percent or more (e.g., about 100 weight percent), based on the total weight of the compounds in the polymerizable composition that are liquid at room temperature.

Polymerization of 1,1-disubstituted alkene compounds using anionic polymerization processes are useful in the bulk polymerization of 1,1-disubstituted alkene compounds and processes which can operate at or near ambient conditions (starting conditions) have been disclosed. Such anionic bulk polymerizations may be initiated using a wide range of initiators, and may even be initiated by contact with certain substrates or by UV light. However, as discussed above, the bulk polymerization may limit the ability to control the structure of the polymer molecules and/or to be able to easily handle the resulting polymer composition or product. These difficulties in bulk polymerization may be particularly pronounced when manufacturing large quantities of polymer, where heat transport issues may occur, especially when there may be shear heat generated by the flow of the high viscosity polymer.

Bulk polymerization of 1,1-disubstituted alkene compounds also present a challenge when attempting to control the structure of the polymer by including one or more comonomers. For example, the high viscosity of the intermediate polymer may present difficulties in preparing a block copolymer (such as by sequential addition of a first monomer system followed by a second monomer system into a reaction vessel). Other problems may arise when attempting to control the structure of a random copolymer, where the reaction rates of the different monomers differ so that the monomers are not uniformly distributed along the length of the polymer molecular. For example, copolymers including one or more 1,1-disubstituted alkene compounds prepared by bulk polymerization are typically expected to have a generally blocky sequence distribution and/or result in polymer molecules having a broad distribution of monomer compositions. As used herein, a copolymer having a generally blocky sequence distribution of monomers may be characterized as having a blockiness index of about 0.7 or less, about 0.6 or less or about 0.5 or less, or about 0.4 or less.

Although emulsion polymerization processes have been employed in free radical polymerization process (see for example, U.S. Pat. No. 7,241,834 B2) to better control the polymer architecture, such processes have not generally been employed in anionic polymerization. In emulsion polymerization systems, the polymerization typically occurs in small micelles that are distributed throughout a carrier liquid (generally water). An emulsifier typically separates the monomer/polymer in the micelles from the carrier liquid. However, in anionic polymerization, many monomers that are capable of polymerization via anionic polymerization are also reactive with water. For example, a Michael addition reaction between 1,1-disubstituted alkene compounds and water is a known reaction which destroys the double bond so that the monomer is no longer polymerizable using anionic polymerization across the double bond. As such, there is a general preference to avoid using water or to diminish the presence of water in the reaction. Similarly, there is a possibility of a Michael addition reaction between the 1,1-disubstituted alkene compound and various surfactants. For these reasons, emulsion polymerization of 1,1-disubstituted alkene compounds has typically been avoided and assumed unsuitable in emulsion polymerization.

When an emulsion polymerization system is employed with free radical polymerization methods, sub-ambient temperatures (e.g., less than 10° C., less than 0° C., or less than −20° C. are typically required to control the reaction. As such, in emulsion polymerization systems it may be necessary to use a carrier liquid that has a low freezing point below −5° C. (such as a mixture of water and a glycol).

Additional difficulties in polymerization of 1,1-disubstituted alkene compounds arise from the possibility of the anionic group of the growing polymer reacting with an acid thereby terminating the reaction. Therefore, one would avoid using an acid in polymerizing 1,1-disubstituted alkene compounds using anionic polymerization.

Prior attempts at anionic polymerization emulsion processes generally have had one or more of the following drawbacks: (1) requirement that the systems have low polymer concentrations (e.g., about 2 weight percent or less, based on the total weight of the emulsion system), (2) have resulted in a prevalence for particle aggregation (even in drop-by-drop methods), (3) have lacked reproducibility for controlling molecular weight distribution, (4) have undesirable reactant by-products, or (5) employ a low reaction temperature.

There is a need for polymerization methods, systems, and resulting polymer compositions or products that allow for improved control of one or more of the following properties of a polymer containing one or more 1,1-disubstituted alkene compounds: the weight average molecular weight, the number average molecular weight, the polydispersity index, the zero-shear viscosity of the polymer (e.g., at one or more temperatures of at least about 20° C. above the melting temperature of the polymer), the viscosity of the polymer system (e.g., the bulk polymer or the polymer emulsion) at room temperature, the sequence distribution of monomers in a random copolymer, or having at least two different polymer blocks covalently bonded (e.g., each containing one or more 1,1-disubstituted alkene compounds). There is also a need for polymerization process which can be scaled-up (e.g., to a reactor of about 20 liters or more, or having a throughput of about 10 kg of polymer per hour or more. There is also a need for processes that result in an emulsion. Such emulsion may be useful for applications such as paints, coatings, finishes, polishes, and adhesives. For example, there may be a need for process and polymer systems that result in an emulsion having a controlled size of emulsion particles.

SUMMARY

One aspect of the disclosure is directed at a process comprising the steps of: agitating a mixture including: about 25 weight percent or more of a carrier liquid, a surfactant (e.g., an emulsifier) and one or more monomers to form micelles of the one or more monomers in the carrier liquid, wherein the one or more monomers includes one or more 1,1-disubstituted alkenes; reacting an activator with at least one of the monomers in the micelle for initiating the anionic polymerization of the one or more monomers; and anionically polymerizing the one or more monomers to a number average molecular weight of about 700 g/mole or more.

Another aspect of the disclosure is directed at a polymer including one or more 1,1-disubstituted alkene monomers. The polymer may be prepared using an emulsion polymerization reaction, such as a reaction according to the teachings herein.

Another aspect of the disclosure is directed at a polymeric composition including one or more 1,1-disubstituted alkene monomers and one or more additives.

Another aspect of the disclosure is directed at a system for polymerizing one or more monomers including a reactor having an agitation device for forming an emulsion; about 30 weight percent or more water; about 10 weight percent or more of one or more monomers including one or more 1,1-disubstituted alkenes; and one or more surfactants. Preferably the agitation device includes a stirring device or a sonication device. The system preferably includes an activator(s) for initiating anionic polymerization of 1,1-disubstituted alkenes.

Another aspect of the disclosure is directed at a block copolymer having a first polymer block including a first primary monomer that is a 1,1-disubstituted alkene compound, wherein the first primary monomer is present at a concentration of about 50 weight percent or more, based on the total weight of the first polymer block, the first polymer block covalently bonded to a second polymer block including a second primary monomer different from the first primary monomer, wherein the second primary monomer is present at a concentration of about 50 weight percent or more, based on the total weight of the second polymer block.

Another aspect of the disclosure is directed at a low molecular weight polymer having a number average degree of polymerization from about 4 to about 50, and the low molecular weight polymer includes about 60 weight percent or more of one or more 1,1-disubstituted alkene compounds, based on the total weight of the low molecular weight polymer. Preferably the low molecular weight polymer includes a primary monomer present at about 90 weight percent or more, based on the total weight of the low molecular weight polymer, and the primary monomer is one of the one or more 1,1-disubstituted alkene compounds.

The methods according to the teachings herein may be employed to produce a polymer including one or more 1,1-disubstituted alkene monomers having improved control of molecular weight, improved control of molecular weight distribution, or both. For example, the emulsion polymerization methods may be employed for controllably producing low molecular weight polymers including a 1,1-disubstituted alkene monomer. The methods according to the teachings herein may be employed to controllably produce high molecular weight polymers including a 1,1-disubstituted alkene. The methods according to the teachings herein may be employed to produce a random copolymer including two or more 1,1-disubstituted alkene monomers having improved control of the monomer sequence distribution. The methods according to the teachings herein may be employed to produce a block copolymer including two different polymer blocks, the block copolymer including one or more 1,1-disubstituted alkene monomers. The methods according to the teachings herein may be employed to produce an emulsion having generally high polymer concentration (e.g., about 10 weight percent or more) and/or having low viscosity. The methods according to the teachings herein may be employed to produce polymers using anionic polymerization with a throughput rate of about 10 kg/hour or more and/or in a reactor system having a volume (e.g., of the emulsion) of about 20 liter or more. For example, the methods according to the teachings herein may better control the temperature during the polymerization, even when using pilot scale or manufacturing scale production (e.g., so that the process is generally free of temperature spikes during polymerization).

BRIEF DESCRIPTION OF THE DRAWINGS

FIG. 3A is taken at an early stage of the polymerization reaction and the peak at 6.45 ppm identifies the presence of unreacted monomer. FIG. 3B is taken at a later stage of the polymerization reaction and there is no detectable peak at 6.45 ppm.

DETAILED DESCRIPTION

Surprisingly, it has been found that a monomer including a 1,1-disubstituted alkene capable of Michael addition with water or moisture in the presence of an acid may be anionically polymerized using an emulsion polymerization process. Furthermore, it has been surprisingly been found that a polymer including a 1,1-disubstituted alkene may be polymerized (e.g., using an anionic polymerization process, such as an anionic emulsion polymerization process according to the teachings herein) to controllably produce polymers (e.g., to produce polymers having controlled molecular weight and/or structure). In the emulsion polymerization process, two or more incompatible phases are formed including a continuous carrier fluid phase and discrete phase including the monomer(s) and/or reaction products from the polymerization of the monomer(s). The emulsion preferably includes a surfactant (i.e., an emulsifying agent) capable of improving the stability of the discrete phases. The methods according to the teachings herein may be used to prepare a homopolymer or a copolymer. For example, the polymer may be a random copolymer or a block copolymer.

Figure 1:
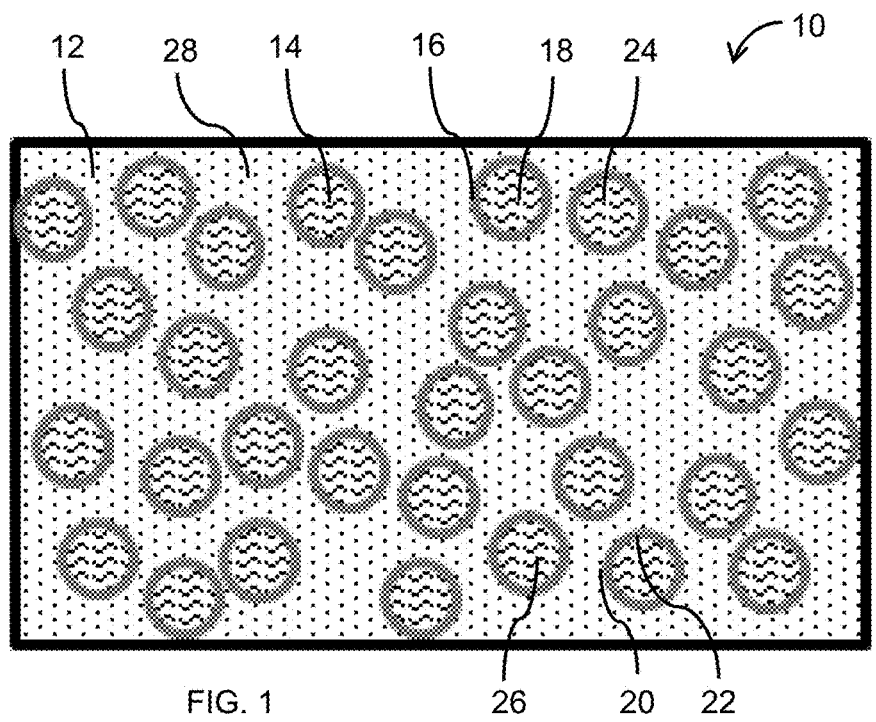
FIG. 1 is a drawing illustrating features of an emulsion system for polymerizating of a polymer including a 1,1-disubstituted alkene monomer according to the teachings herein using anionic polymerization.

FIG. 1 illustrates features that may be employed in an emulsion system according to the teachings herein. The emulsion system 10 includes a continuous liquid phase 12 and a dispersed phase 14. The dispersed phase may be in the form of micelles. The dispersed phase 14 includes a surfactant 16, which may be present as a surfactant layer 16. The dispersed phase 14 has an interior that includes a monomer and/or a polymer 26. It will be appreciated that prior to a polymerization reaction, the dispersed phase may include monomer 26 and be substantially free of any polymer 26. After a polymerization reaction begins, the dispersed phase may include both monomer and polymer 26. The monomer may be completely converted so that eventually the dispersed phase includes polymer 26 and is substantially or entirely free of monomer. The surfactant layer 16 may have an inner surface 22 and an outer surface 20. The inner surface 22 may contact the monomer and/or the polymer 26. The outer surface 20 may contact the continuous liquid phase 12. The continuous liquid phase 12 may include or consist substantially (e.g., about 90 volume percent or more or about 98 volume percent or more based on the total volume of the continuous liquid phase) of a carrier liquid 28. The carrier liquid 28 preferably includes water, and more preferably deionized water. The monomer 26 and/or polymer 26 preferably includes one or more 1,1-disubstituted alkene compounds.

The monomer includes one or more monomers capable of Michael addition with water or moisture in the presence of an acid. The monomer typically includes one or more 1,1-disubstituted alkene compounds (e.g., one or more 1,1-disubstituted ethylene compounds. The 1,1-disubstituted alkene preferably is a primary monomer (i.e., a monomer present at 50 weight percent or more of a polymer block or of an entire polymer). 1,1-disubstituted alkene compounds are compounds (e.g., monomers) wherein a central carbon atom is doubly bonded to another carbon atom to form an ethylene group. The central carbon atom is further bonded to two carbonyl groups. Each carbonyl group is bonded to a hydrocarbyl group through a direct bond or an oxygen atom. Where the hydrocarbyl group is bonded to the carbonyl group through a direct bond, a keto group is formed. Where the hydrocarbyl group is bonded to the carbonyl group through an oxygen atom, an ester group is formed. The 1,1-disubstituted alkene preferably has a structure as shown below in Formula I, where $X^1$ and $X^2$ are an oxygen atom or a direct bond, and where $R^1$ and $R^2$ are each hydrocarbyl groups that may be the same or different. Both $X^1$ and $X^2$ may be oxygen atoms, such as illustrated in Formula IIA, one of $X^1$ and $X^2$ may be an oxygen atom and the other may be a direct bond, such as shown in Formula IIB, or both $X^1$ and $X^2$ may be direct bonds, such as illustrated in Formula IIC. The 1,1-disubstituted alkene compounds used herein may have all ester groups (such as illustrated in Formula IIA), all keto groups (such as illustrated in Formula IIB) or a mixture thereof (such as illustrated in Formula IIC). Compounds with all ester groups are preferred due to the flexibility of synthesizing a variety of such compounds.

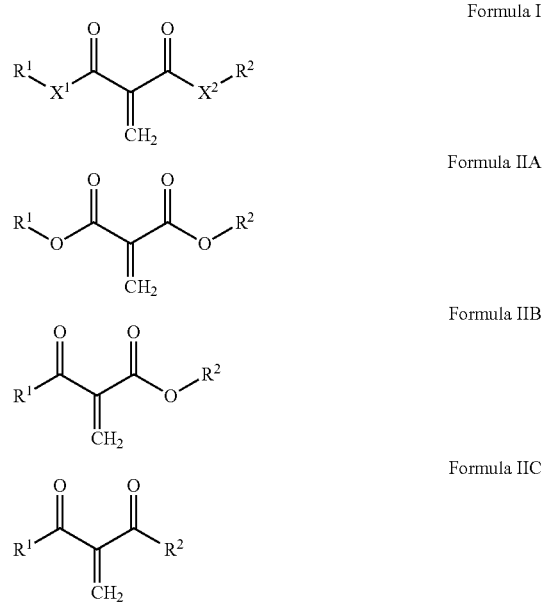

One or more as used herein means that at least one, or more than one, of the recited components may be used as disclosed. Nominal as used with respect to functionality means the theoretical functionality, generally this can be calculated from the stoichiometry of the ingredients used. Generally, the actual functionality is different due to imperfections in raw materials, incomplete conversion of the reactants and formation of by-products. Durability in this context means that the composition once cured remains sufficiently strong to perform its designed function, in the embodiment wherein the cured composition is an adhesive, the adhesive holds substrates together for the life or most of the life of the structure containing the cured composition. As an indicator of this durability, the curable composition (e.g., adhesive) preferably exhibits excellent results during accelerated aging. Residual content of a component refers to the amount of the component present in free form or reacted with another material, such as a polymer. Typically, the residual content of a component can be calculated from the ingredients utilized to prepare the component or composition. Alternatively, it can be determined utilizing known analytical techniques. Heteroatom means nitrogen, oxygen, sulfur and phosphorus, more preferred heteroatoms include nitrogen and oxygen. Hydrocarbyl as used herein refers to a group containing one or more carbon atom backbones and hydrogen atoms, which may optionally contain one or more heteroatoms. Where the hydrocarbyl group contains heteroatoms, the heteroatoms may form one or more functional groups well known to one skilled in the art. Hydrocarbyl groups may contain cycloaliphatic, aliphatic, aromatic or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. One or both hydrocarbyl groups may consist of one or more carbon atoms and one or more hydrogen atoms. As used herein percent by weight or parts by weight refer to, or are based on, the weight of the emulsion composition unless otherwise specified.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

1,1-disubstituted alkene compound means a compound having a carbon with a double bond attached thereto and which is further bonded to two carbon atoms of carbonyl groups. A preferred class of 1,1-disubstituted alkene compounds are the methylene malonates which refer to compounds having the core formula

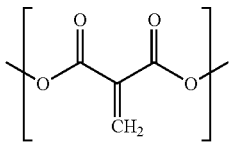

The term "monofunctional" refers to 1,1-disubstituted alkene compounds or a methylene malonates having only one core formula. The term "difunctional" refers to 1,1-disubstituted alkene compounds or a methylene malonates having two core formulas bound through a hydrocarbyl linkage between one oxygen atom on each of two core formulas. The term "multifunctional" refers to 1,1-disubstituted alkene compounds or methylene malonates having more than one core formula which forms a chain through a hydrocarbyl linkage between one oxygen atom on each of two adjacent core formulas. The term "latent acid-forming impurities" or "latent acid-forming impurity" refers to any impurity that, if present along with the 1,1-disubstituted alkene compounds or methylene malonates, will with time be converted to an acid. The acid formed from these impurities may result in overstabilization of the 1,1-disubstituted alkene compounds, thereby reducing the overall quality and reactivity of the compounds. The term "ketal" refers to a molecule having a ketal functionality; i.e., a molecule containing a carbon bonded to two —OR groups, where O is oxygen and R represents any alkyl group. The terms "volatile" and "non-volatile" refers to a compound which is capable of evaporating readily at normal temperatures and pressures, in the case of volatile; or which is not capable of evaporating readily at normal temperatures and pressures, in the case of non-volatile. As used herein, the term "stabilized" (e.g., in the context of "stabilized" 1,1-disubstituted alkene compounds or monomer compositions comprising same) refers to the tendency of the compounds (or the monomer compositions), prior to activation with an activator, to substantially not polymerize with time, to substantially not harden, form a gel, thicken, or otherwise increase in viscosity with time, and/or to substantially show minimal loss in cure speed (i.e., cure speed is maintained) with time. As used herein, the term "shelf-life" (e.g., as in the context of 1,1-disubstituted alkene compounds having an improved "shelf-life") refers to the 1,1-disubstituted alkene compounds which are stabilized for a given period of time; e.g., 1 month, 6 months, or even 1 year or more.

The hydrocarbyl groups (e.g., $R^1$ and $R^2$), each comprise straight or branched chain alkyl, straight or branched chain alkyl alkenyl, straight or branched chain alkynyl, cycloalkyl, alkyl substituted cycloalkyl, aryl, aralkyl, or alkaryl. The hydrocarbyl group may optionally include one or more heteroatoms in the backbone of the hydrocarbyl group. The hydrocarbyl group may be substituted with a substituent that does not negatively impact the ultimate function of the monomer or the polymer prepared from the monomer. Preferred substituents include alkyl, halo, alkoxy, alkylthio, hydroxyl, nitro, cyano, azido, carboxy, acyloxy, and sulfonyl groups. More preferred substituents include alkyl, halo, alkoxy, alylthio, and hydroxyl groups. Most preferred substituents include halo, alkyl, and alkoxy groups.

As used herein, alkaryl means an alkyl group with an aryl group bonded thereto. As used herein, aralkyl means an aryl group with an alkyl group bonded thereto and include alkylene bridged aryl groups such as diphenyl methyl groups or diphenyl propyl groups. As used herein, an aryl group may include one or more aromatic rings. Cycloalkyl groups include groups containing one or more rings, optionally including bridged rings. As used herein, alkyl substituted cycloalkyl means a cycloalkyl group having one or more alkyl groups bonded to the cycloalkyl ring.

Preferred hydrocarbyl groups include 1 to 30 carbon atoms, more preferably 1 to 20 carbon atoms, and most preferably 1 to 12 carbon atoms. Preferred hydrocarbyl groups with heteroatoms in the backbone are alkyl ethers having one or more alkyl ether groups or one or more alkylene oxy groups. Preferred alkyl ether groups are ethoxy, propoxy, and butoxy. Preferably such compounds contain from about 1 to about 100 alkylene oxy groups and more preferably about 1 to about 40 alkylene oxy groups and more preferably from about 1 to about 12 alkylene oxy groups, and most preferably from about 1 to about 6 alkylene oxy groups.

One or more of the hydrocarbyl groups (e.g., $R^1$, $R^2$, or both), preferably includes a $C_{1-15}$ straight or branched chain alkyl, a $C_{1-15}$ straight or branched chain alkenyl, a $C_{5-18}$ cycloalkyl, a $C_{6-24}$ alkyl substituted cycloalkyl, a $C_{4-18}$ aryl, a $C_{4-20}$ aralkyl, or a $C_{4-20}$ aralkyl. More preferably, the hydrocarbyl group, includes a $C_{1-8}$ straight or branched chain alkyl, a $C_{5-12}$ cycloalkyl, a $C_{6-12}$ alkyl substituted cycloalkyl, a $C_{4-18}$ aryl, a $C_{4-20}$ aralkyl, or a $C_{4-20}$ aralkyl.

Preferred alkyl groups include methyl, propyl, isopropyl, butyl, tertiary butyl, hexyl, ethyl pentyl, and hexyl groups. More preferred alkyl groups include methyl and ethyl. Preferred cycloalkyl groups include cyclohexyl and fenchyl. Preferred alkyl substituted groups include menthyl and isobornyl.

Most preferred hydrocarbyl groups attached to the carbonyl group include methyl, ethyl, propyl, isopropyl, butyl, tertiary, pentyl, hexyl, octyl, fenchyl, menthyl, and isobornyl.

Particularly preferred monomers include methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-N-propyl methylene malonate, ethyl hexyl methylene malonate, methyl fenchyl methylene malonate, ethyl fenchyl methylene malonate, 2 phenylpropyl ethyl methylene malonate, 3 phenylpropyl ethyl methylene malonate, and dimethoxy ethyl methylene malonate.

Some or all of the 1,1-disubstituted alkenes can also be multifunctional having more than one core unit and thus more than one alkene group. Exemplary multifunctional 1,1-disubstituted alkenes are illustrated by the formula:

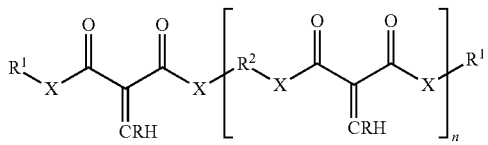

wherein $R^1$, $R^2$ and X are as previously defined; n is an integer of 1 or greater; and R is a hydrocarbyl group, and the 1,1-disubstituted alkene has n+1 alkenes. Preferably n is 1 to about 7, and more preferably 1 to about 3, and even more preferably 1. In exemplary embodiments $R^2$ is, separately in each occurrence, straight or branched chain alkyl, straight or branched chain alkenyl, straight or branched chain alkynyl, cycloalkyl, alkyl substituted cycloalkyl, aryl, aralkyl, or alkaryl, wherein the hydrocarbyl groups may contain one or more heteroatoms in the backbone of the hydrocarbyl group and may be substituted with a substituent that does not negatively impact the ultimate function of the compounds or polymers prepared from the compounds. Exemplary substituents are those disclosed as useful with respect to $R^1$. In certain embodiments $R^2$ is, separately in each occurrence, $C_{1-15}$ straight or branched chain alkyl, $C_{2-15}$ straight or branched chain alkenyl, $C_{5-18}$ cycloalkyl, $C_{6-24}$ alkyl substituted cycloalkyl, $C_{4-18}$ aryl, $C_{4-20}$ aralkyl or $C_{4-20}$ aralkyl groups. In certain embodiments $R^2$ is separately in each occurrence $C_{1-8}$ straight or branched chain alkyl, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups.

It will be appreciated according to the teaching herein, the one or more monomer may include a comonomer that is a 1,1-disubstituted alkene compound having a hydrocarbyl group bonded to each of the carbonyl groups through a direct bond (e.g., a carbon-carbon bond) or an oxygen atom, such as a monomer having one or more features described above. If included, a comonomer may optionally be a monomer that is not a 1,1-disubstituted alkene compound. Any comonomer capable of anionic polymerization may be employed. For example, the comonomer may be capable of forming a random copolymer with a 1,1-disubstituted alkene compound, capable of forming a block copolymer with a 1,1-disubstituted alkene compound, or both.

The 1,1-disubstituted alkene compound preferably is prepared using a method which results in a sufficiently high purity so that it can be polymerized. The purity of the 1,1-disubstituted alkene compound may be sufficiently high so that 70 mole percent or more, preferably 80 mole percent or more, more preferably 90 mole percent or more, even more preferably 95 mole percent or more, and most preferably 99 mole percent or more of the 1,1-disubstituted alkene compound is converted to polymer during a polymerization process. The purity of the 1,1-disubstituted alkene compound preferably is about 85 mole percent or more, more preferably about 90 mole percent or more, even more preferably about 93 mole percent or more, even more preferably about 95 mole percent or more, even more preferably about 97 mole percent or more, and most preferably about 97 mole percent or more, based on the total weight of the 1,1-disubstituted alkene compound. If the 1,1-disubstitute alkene compound includes impurities, preferably about 40 mole percent or more, more preferably about 50 mole percent or more of the impurity molecules are the analogous 1,1-disubstituted alkane compound. The concentration of any impurities having a dioxane group preferably is about 2 mole percent or less, more preferably about 1 mole percent or less, even more preferably about 0.2 mole percent or less, and most preferably about 0.05 mole percent or less, based on the total weight of the 1,1-disubstituted alkene compound. The total concentration of any impurity having the alkene group replaced by an analogous hydroxyalkyl group (e.g., by a Michael addition of the alkene with water), preferably is about 3 mole percent or less, more preferably about 1 mole percent or less, even more preferably about 0.1 mole percent or less, and most preferably about 0.01 mole percent or less, based on the total moles in the 1,1-disubstituted alkene compound. Preferred 1,1-disubstituted alkene compounds are prepared by a process including one or more (e.g., two or more) steps of distilling a reaction product or an intermediate reaction product (e.g., a reaction product or intermediate reaction product of a source of formaldehyde and a malonic acid ester).

The polymerization process preferably includes one or more surfactants for forming an emulsion having micelles or a discrete phase including a monomer (e.g., a 1,1-disubstituted alkene compound) distributed throughout a continuous phase (e.g., a continuous phase including a carrier liquid). The surfactant may be an emulsifier, a defoamer, or a wetting agent. The surfactant preferably is present in a sufficient quantity so that a stable emulsion is formed by mixing or otherwise agitating a system including the monomer and carrier liquid. The surfactants according to the teachings herein include one or more surfactants for improving the stability of emulsion (i.e., for improving the stability of the dispersed phase in the carrier liquid phase). The surfactant and/or the amount of surfactant is preferably selected so that all of the monomer micelles are covered by a layer of the surfactant.

The surfactant may include a first end that is hydrophobic and an opposing second end that is hydrophilic. The surfactant may include one segment (e.g., one end) of the surfactant having a dipole moment (in absolute value) greater than about 0.1 debye.

The surfactant may include an amphoteric surfactant, a nonionic surfactant, or any combination thereof. The surfactant preferably is free of anionic surfactants during the polymerization process.

Surfactants that may be employed include alkyl polysaccharides, alkylamine ethoxylates, amine oxides, castor oil ethoxylates, ceto-oleyl, ceto-stearyl, decyl alcohol ethoxylates, dinonyl phenol ethoxylates, dodecyl phenol ethoxylates, end-capped ethoxylates, ethoxylated alkanolamides, ethylene glycol esters, fatty acid alkanolamides, fatty alcohol alkoxylates, lauryl, mono-branched, nonyl phenol ethoxylates, octyl phenol ethoxylates, random copolymer alkoxylates, sorbitan ester ethoxylates, stearic acid ethoxylates, synthetic, tall oil fatty acid ethoxylates, tallow amine ethoxylates, alkyl ether phosphates, alkyl phenol ether phosphates, alkyl phenol ether sulfates, alkyl naphthalene sulfonates, condensed naphthalene sulfonates, aromatic hydrocarbon sulphonic acids, fatty alcohol sulfates, alkyl ether carboxylic acids and salts, alkyl ether sulfates, mono-alkyl sulphosuccinamates, di-alkyl sulphosuccinates, alkyl phosphates, alkyl benzene sulphonic acids and salts, alpha olefin sulfonates, condensed naphthalene sulfonates, polycarboxylates, alkyl dimethylamines, alkyl amidopropylamines, quaternised amine ethoxylates, quaternary ammonium compounds, and mixtures or combinations thereof.

Non-limiting examples of amphoteric surfactants that may be employed include amine oxide surfactants, sultaine surfactants, betaine surfactants, or any combination thereof. Preferred sultaine and betaine surfactants include hydroxysultaines and hydroxybutaines. Without limitation, exemplary amphoteric surfactants that may be employed include cocamine oxide, cocoamidopropylamine oxide, cetamine oxide, decylamine oxide, lauramine oxide, myristylamine oxide, cetyl amine oxide, steramine oxide, cocamidopropyl hydroxysultaine, capryl/capramidopropyl betaine, cocamidopropyl betaine, cetyl betaine, cocamidopropyl betaine, laurylamidopropyl betaine, or any combination thereof.

Non-limiting examples of cationic surfactants include quaternary ammonium chloride surfactants, quaternary ammonium methyl sulfate surfactants, ester quaternarie surfactants, or any combination thereof. Without limitation, exemplary cationic surfactants that may be employed include cetrimonium chloride, stearalkonium chloride, olealkonium chloride, stearamidopropalkonium chloride, alkyl dimethyl benzyl ammonium chlorides, alkyl dimethyl ethylbenzyl ammonium chlorides, didecyl dimethyl ammonium chloride, dialkyl dimethyl ammonium chloride, benzalkonium chloride, methyl bis(hydrogenated tallow amidoethyl)-2-hydroxyethyl amonium methyl sulfate, methyl bis(tallowamido ethyl)-2-hydroxyethyl ammonium methyl sulfate, methyl bis(tallowamido ethyl)-2-tallow imidazolinium methyl sulfate, dialkyl ammonium methosulfate, dialkylester ammonium methosulfate, dipalmitoylethyl hydroxyethylmmonium methosulfate, dialkyl ammonium methosulfate, dialkylester ammonium methosulfate, methyl bis[ethyl (tallowate)]-2-hydroxyethyl ammonium methyl sulfate, methyl bis[ethyl (tallowate)]-2-hydroxyethyl ammonium methyl sulfate, or any combination thereof.

Non-limiting examples of nonionic surfactants include alkoxylate surfactants, amide surfactants, ester surfactants, ethoxylate surfactants, lactate surfactants, triglyceride surfactants, or any combination thereof. Without limitation, exemplary nonionic surfactants that may be employed include polyalkoxylated alphatic bases, polyalkoxylated amides, alkylphenol alkoxylates, alkylphenol block copolymers, alkyl phenol ethoxylates, polyalkylene oxide block copolymers, glyceryl cocoate, alcohol alkoxylates, butyl based block copolymers, polyalkylene oxide block copolymer, N, N-dimethyldecanamide (N, N-dimethylcapramide), N, N-dimethyloctanamide (N, N-dimethylcaprylamide), fatty alkanolamides, oleyl diethanolamide, lauryl diethanolamide, coco diethanolamide, fatty diethanolamides, polyethylene glycol cocamides, polyethylene glycol lauramides, lauryl monoethanolamide, myristyl monoethanolamide, coco monoisopropanolamide, alkyl ether phosphates, phosphate esters, glyceryl monostearate, glycerol monooleate, polyglyceryl decaoleates, polyglycerol esters, polyglycerol polyricinoleates, neutralized alcohol phosphates, capric triglyceride, caprylic triglyceride, tridecyl alcohol phosphate ester, nonylphenol ethoxylate phosphate ester, trimethylopropane tricaprylate tricaprate polyol ester, methyl caprylate/caprate, methyl laurate, methyl myristate, methyl palmitate, methyl oleate, alcohol phosphates, trimethylolpropane tricaprylate/caprate polyol ester, pentaerythritol tricaprylate/caprate polyol ester, pentaerythrityl tetracaprylate/tetracaprate, nonylphenol phosphate ester, phosphate esters of an alkyl polyethoxyethanol, canola oil methyl ester, soybean oil methyl ester, pentaerythritol tetracaprylate/caprate, trimethylolpropane tricaprylate/caprate, amine neutralized phosphate ester, fatty alkyl ethoxylates, alcohol ethoxylates, fatty acid ethoxylates, tallow amine ethoxylates, octyl phenol ethoxylates, nonyl phenol ethoxylate, castor oil ethoxylate, polyalkoxylated alphatic bases, polyalkoxylated amides, octyl phenol ethoxylate, tristyrylphenol ethoxylate, ammonium salt of ethoxylated polyarylphenol sulfates, tristyrylphenol ethoxylate phosphate ester, potassium salt of tristyrylphenol ethoxylate phosphate ester, ethoxylated coco amine, sorbital trioleate ethoxylate, sorbital monooleate ethoxylate, lauryl lactyl lactate, capric triglyceride, caprylic triglyceride, hydrogenated vegetable oil, or any combination thereof.

One example of a preferred surfactant (e.g., an emulsifier) is an ethoxylate, such as an ethoxylated diol. For example, the surfactant may include 2,4,7,9-tetramethyl-5-decyne-4, 7-diol ethoxylate. The surfactant may include a poly(alkene glycol). Another example of a preferred surfactant is a poly(ethylene glycol)-block-poly(propylene glycol)-block-poly(ethylene glycol) copolymer. Another example of a preferred surfactant is a surfactant including an alcohol, an ethoxylated alcohol, or both. For example, the surfactant may include CARBOWET® 138 nonionic surfactant (including alkyl alcohol, polyethylene glycol, ethoxylated C9-C11 alcohols). Another example of a preferred surfactant is a surfactant including a sorbitan, a sorbitol, or a polyoxyalkene. For example, the surfactant may include sorbitan monopalmitate (nonionic surfactant). Other examples of preferred surfactants include branched polyoxyethylene (12) nonylphynyl ether (IGEPAL® CO-720) and poly(ethylene glycol) sorbitol hexaoleate (PEGSH).

The amount of the surfactant (e.g., the amount of the emulsifier) preferably is sufficient to form a layer that substantially encapsulates the monomer and subsequent polymer particles. The amount of surfactant preferably is sufficient so that the discrete phase has a diameter of about 10 mm or less, about 1 mm or less, about 300 µm or less, or about 100 µm or less. The amount of the surfactant is preferably sufficient so that the discrete phase has a diameter of about 0.01 µm or more, about 0.1 µm or more, about 1 µm or more, about 10 µm or more, or about 50 µm or more. The concentration of the surfactant may be about 0.001 weight percent or more, preferably about 0.01 weight percent or more, more preferably about 0.1 weight percent or more, and most preferably about 0.5 weight percent or more, based on the total weight of the emulsion. The concentration of the surfactant may be about 15 weight percent or less, preferably about 10 weight percent or less, and more preferably about 6 weight percent or less, and most preferably about 3 weight percent or less, based on the total weight of the emulsion. The weight ratio of the surfactant to the total weight of the monomer and polymer in the emulsion (e.g., at the end of the polymerization process) preferably is about 0.0001 or more, more preferably about 0.002 or more, even more preferably about 0.005 or more, and most preferably about 0.01 or more. The weight ratio of the surfactant to the total weight of the monomer and polymer in the emulsion (e.g., at the end of the polymerization process) preferably is about 5 or less (i.e., about 5:1 or less), more preferably about 1 or less, even more preferably about 0.5 or less, and most preferably about 0.1 or less.

The surfactant is preferably added prior to the polymerization process. However, it will be appreciated that one or more surfactants may be added following a polymerization process (e.g., following an emulsion polymerization process). For example, a surfactant may be added following a polymerization process to stabilize an emulsion (such as for long term stability of about 1 week or more, about 1 month or more, or about 3 months or more).

The carrier liquid may be any liquid which is not a solvent for the one or more monomers. The carrier liquid may include water, a glycol, an alcohol, a ketone, an alkane, an aprotic compound, an ester, an ether, acetone, an acetate, a hydrofuran, a phenyl or a compound including one or more aryl groups, or any combination thereof. More preferred carrier liquids include water, a glycol, an alcohol, a ketone, or any combination thereof. Even more preferred carrier liquids include water, ethylene glycol, methanol, a monoalkyl ether of ethylene glycol, or any combination thereof. Preferred carrier liquids include a single compound or include a mixture of compounds that are miscible, e.g., so that the carrier liquid is a single phase. The carrier liquid may have a freezing point of about 10° C. or less, and preferably about 0° C. or less.

Preferably the carrier liquid includes, consists essentially of, or consists entirely of water. For example, the carrier liquid may consist entirely of deionized water. The quality of the water may play an important role. For example, the presence of foreign ions can interfere with the initiation process, efficacy of the surfactant(s), and subsequent pH control. Preferably, the concentration of foreign ions (i.e., ions other than H3O+ and OH-) in the water is sufficiently low so that the water meets the requirements of class 3 or better, class 2 or better, or class 1 or better, as measured according to ISO 3696. The conductivity of the water preferably is about 10 mS/m or less, more preferably about 1 mS/m or less, even more preferably about 100 µS/m or less, and most preferably about 10 µS/m or less. The conductivity of the water may be about 0 or more, about 0.1 µS/m or more, or about 1 µS/m or more.

The emulsion polymerization may be initiated using an activator capable of initiating anionic polymerization of the 1,1-disubstituted alkene containing compound. The activator may be a compound that is a nucleophile or a compound that forms a nucleophile. Examples of activators (i.e., initiators), which may be employed, include ionic metal amides, hydroxides, cyanides, phosphines, alkoxides, amines and organometallic compounds (such as alkyllithium compounds), and metal benzoates. The polymerization activator may have one or more of the features (e.g., include one or any combinations of the activating agents and/or polymerization activators, include an activating agent at a concentration or concentration range, or include a process step) as described in US patent Application publication US 2015/0073110 A1, published on Mar. 12, 2015, incorporated herein by reference (e.g., see paragraphs 0024 to 0050). By way of example, the activator may include, consist essentially of, or consist entirely of one or more metal benzoates, such as sodium benzoate. As an alternative to using an activator, the polymerization may be activated using a source of radiation, preferably UV light. The molecular weight of the polymer may be adjusted by adjusting the molar ratio of the monomer to the activator. Preferably the molar ratio of the monomer to activator is about 25 or more, about 50 or more, about 100 or more, about 500 or more, or about 1,000 or more. The molar ratio of the monomer to the activator preferably is about 100,000 or less, about 50,000 or less, about 10,000 or less, or about 2,000 or less.

According to certain embodiments, a suitable polymerization activator can generally be selected from any agent that can initiate polymerization substantially upon contact with a selected polymerizable composition. In certain embodiments, it can be advantageous to select polymerization initiators that can induce polymerization under ambient conditions and without requiring external energy from heat or radiation. In embodiments wherein the polymerizable composition comprises one or more 1,1-disubstituted alkene compounds, a wide variety of polymerization initiators can be suitable including most nucleophilic initiators capable of initiating anionic polymerization. For example, suitable initiators include alkali metal salts, alkaline earth metal salts, ammonium salts, amine salts, halides (halogen containing salts), metal oxides, and mixtures containing such salts or oxides. Exemplary anions for such salts include anions based on halogens, acetates, benzoates, sulfur, carbonates, silicates and the like. The mixtures containing such salts can be naturally occurring or synthetic. Specific examples of suitable polymerization initiators for 1,1-disubstituted alkene compounds can include ionic compounds such as sodium silicate, sodium benzoate, and calcium carbonate. Additional suitable polymerization initiators for such polymerizable compositions are also disclosed in U.S. Patent Application Publication No. 2015/0073110, which is hereby incorporated by reference.

The emulsion and/or one or more of the monomers (e.g., the 1,1-disubstituted alkene compounds) may further contain other components to stabilize the monomer prior to exposure to polymerization conditions or to adjust the properties of the final polymer for the desired use.

Prior to the polymerization reaction, one or more inhibitors may be added to reduce or prevent reaction of the monomer.

An acid containing compound may be employed in the emulsion polymerization process. With various monomers, the use of an acid containing compound may be employed to reduce the reaction rate, decrease the polydispersity, or both. An additional benefit is the formation of stable monomer droplets and polymer particles (i.e., decreasing likely coalescence and/or aggregation). When the concentration of the acid containing compound is too high, the polymerization reaction may be too slow for commercial viability.

When the concentration of the acid containing compound is too low, the polymerization reaction may result in a polymer having high polydispersity index. The acid containing compound may be a compound (e.g., an emulsifier or other surfactant) capable of forming an emulsion of the monomer in the carrier liquid without the use of other surfactants. However, if the acid containing compound is capable of functioning as a surfactant, it is preferred that a second surfactant (such as a surfactant that does not form an acid) be employed. The acid containing compound may be an organic compound having one or more acid groups. For example, the acid containing compound may include one or more acid groups having a sulfur, phosphorous, chlorine, or bromine, fluorine or nitrogen atom. The acid containing compound preferably includes one or more nitrogen atoms (such as in a nitrate or nitrite group) and/or one or more sulfur atoms (such as in a sulfonate group). A particularly preferred acid containing compound is 4-dodecylbenzenesulfonic acid (DBSA). It is known that DBSA, in an incompatible or biphasic mixture, will orient in such a way as to provide protons at the monomer-water interface (e.g., primarily on the water side of the interface) thereby inducing functional inhibition or termination of the reactive monomer and/or propagating polymer chain. It will be appreciated that other acid containing surfactants may similarly affect the initiation, propagation, or termination of the polymer. Preferably, the weight ratio of the acid containing compound to the total weight of the surfactant is about 0.6 or less, more preferably about 0.3 or less, even more preferably 0.1 or less, and most preferably about 0.05 or less. Preferably, the weight ratio of the acid containing compound to the total weight of the surfactant is about 0.001 or more, more preferably about 0.005 or more, and most preferably about 0.01 or more. The weight ratio of the acid containing compound to the amount of the monomer employed for a polymerization step (e.g., for polymerizing a first polymer block) preferably is about 0.00005 or more, more preferably about 0.0002 or more and most preferably about 0.0005 or more. The weight ratio of the acid containing compound to the amount of the monomer employed for a polymerization step (e.g., for polymerizing a first polymer block) preferably is about 0.2 or less, more preferably about 0.04 or less, and most preferably about 0.005 or less.

The polymerization process may include a step of applying shear forces or sonication to a mixture including at least the surfactant and the carrier fluid for forming an emulsion. For example, the process may include stirring or otherwise agitating the mixture for creating the emulsion.

The polymerization process may be a batch process (e.g., using a single batch reactor or a series of batch reactors). The polymerization process may be in a continuous process, such as a process that transports an emulsion along the length of a reactor. In a batch process, or in a continuous process, all of the monomer may be added at a single stage (e.g., prior to the addition of the polymerization activator, or at or near the start of the polymerization reaction) or may be added at multiple stages in the polymerization reaction.

The polymerization process may be employed for polymerization of a homopolymer or a copolymer, such as a random copolymer or a block copolymer. The homopolymer or copolymer includes one or more 1,1-disubstituted alkene containing compounds according to the teachings herein. Preferably, the amount of the 1,1-disubstituted alkene containing compounds in the polymer is about 5 weight percent or more, more preferably about 30 weight percent or more, even more preferably about 50 weight percent or more, even more preferably about 70 weight percent or more, based on the total weight of the emulsion polymer. For example, one or more of the polymer blocks may consist essentially of, or entirely of the 1,1-disubstituted alkene containing compounds.

A multi-stage addition of monomer may be employed for polymerization of a block copolymer having polymer blocks with different compositions. For example, a block copolymer may have a first polymer block, (block A), and a second polymer block (block B). The block copolymer may have 2 or more blocks or 3 or more blocks. The A block and B block may include at least one monomer that is the same (however at different concentrations), or may include only monomers that are different. For example, the A block may be a homopolymer of a first monomer, and the B block may include one or more second monomers which are each different from the first monomer. The first polymer block may be a homopolymer or a copolymer (e.g., a random copolymer). The second polymer block may be a homopolymer or a copolymer (e.g., a random copolymer). The first polymer block and the second polymer block preferably each include one or more 1,1-disubstituted alkene containing compounds according to the teachings herein. Preferably, the amount of the 1,1-disubstituted alkene containing compounds in the first polymer block and/or in the second polymer block may be about 30 weight percent or more, preferably about 50 weight percent or more, even more preferably about 70 weight percent or more, based on the total weight of the polymer block. For example, one or more of the polymer blocks may consist essentially of, or entirely of the 1,1-disubstituted alkene containing compounds. It will be appreciated that one or more blocks may be substantially or entirely free of any 1,1-disubstituted alkene containing compounds. For example, one or more of the polymer blocks may include one or more conjugated diene monomers and/or one or more styrenic monomers.

During the polymerization process, the emulsion is preferably stirred or otherwise agitated to create and/or maintain the micelle structure. For example, the emulsion including the monomer, the emulsifying agent, and the carrier liquid may be mixed at a rate of 10 rpm or more, 50 rpm or more, 200 rpm or more, or 1,000 rpm or more.

The emulsion polymerization process preferably includes a reaction temperature at which the partial pressure of the carrier liquid is generally low. For example, the partial pressure of the carrier liquid may be about 400 Torr or less, about 200 Torr or less, about 100 Torr or less, about 55 Torr or less, or about 10 Torr or less. The reaction temperature preferably is about 80° C. or less, more preferably about 70° C. or less, even more preferably about 60° C. or less, even more preferably about 55° C. or less, even more preferably about 45° C. or less, even more preferably about 40° C. or less, and most preferably about 30° C. or less. The reaction temperature typically is sufficiently high that the carrier liquid is in a liquid state. For example, the reaction temperature may be about −30° C. or more, about −10° C. or more, or about 10° C. or more, or about 15° C. or more.

When polymerizing a 1,1-disubstituted alkene compound, it may be desirable to add one or more acid compounds to the emulsion, to the monomer, or both, so that the initial pH of the emulsion is about 7 or less, about 6.8 or less, about 6.6 or less, or about 6.4 or less. It is believed that such an initial acidic condition may be beneficial for controlling or otherwise limiting the initiation of the monomer. For example, the 1,1-disubstituted alkene compound may be a compound that will auto-initiate under basic conditions and the use of an acid condition may prevent or minimize such auto-initiation. The acidic condition preferably is maintained throughout the polymerization process. If the pH is too low, the reaction rate may be low or the reaction may be terminated. Preferably, the pH during the reaction is about 5 or more, more preferably about 5.5 or more, even more preferably about 5.9 or more, and most preferably about 6 or more. It will be appreciated that following the polymerization process the pH may be adjusted to increase or decrease the pH. Preferably following the polymerization process, the pH is reduced so that the difference between the initial pH (during the reaction) and a later pH is about 0.2 or more, more preferably about 0.3 or more, even more preferably about 0.4 or more and most preferably about 0.5 or more. For example, the process may include a step of decreasing the pH to a range of about 4.0 to about 6.2, to a range of about 4.5 to about 6.0, to a range of about 5.0 to about 6.0, or to a range of about 5.3 to about 5.9. Following a step of polymerizing a 1,1-disubstituted alkene compound and/or following a step of separating the polymer from any residual monomer, the process may include a step of increasing the pH (e.g. to about 6.5 or more, to about 6.9 or more, or to about 7 or more).

The concentration of the carrier liquid in the emulsion composition preferably is sufficiently high so that the micelles of the emulsion do not agglomerate. The concentration of the carrier liquid may be sufficiently high so that the carrier liquid functions as a heat sink and minimizes any spikes in temperature during polymerization to about 30° C. or less, more preferably about 15° C. or less, even more preferably about 10° C. or less, and most preferably about 5° C. or less. The concentration of the carrier liquid may be sufficiently high so that the emulsion is capable of flowing even after the polymerization reaction is complete. For example, the ratio of the zero shear viscosity (measured at 25° C.) of the emulsion to the zeros shear viscosity of the polymer produced by the emulsion polymerization process may be about 0.2 or less, about 0.1 or less, about 0.02 or less, or about 0.005 or less, or about 0.001 or less. The viscosity ratio may be 0 or more. Preferably, the concentration of the carrier liquid is about 25 weight percent or more, even more preferably about 30 weight percent or more, even more preferably about 35 weight percent or more, and most preferably about 40 weight percent or more. The concentration of the carrier liquid should be sufficiently low so that the polymerization process is economical. Preferably the concentration of the carrier liquid is about 98 weight percent or less, more preferably about 80 weight percent or less, even more preferably about 70 weight percent or less, and most preferably about 65 weight percent or less.

The emulsion polymerization process may be stopped prior to the completion of the polymerization reaction or may be continued until the completion of the polymerization reaction. Preferably, the reaction rate is sufficiently high and/or the reaction time is sufficiently long so that the polymerization reaction is substantially complete. For example the conversion of the monomer to polymer may be about 80 weight percent or more, about 90 weight percent or more, about 95 weight percent or more, about 98 weight percent or more, about 99 weight percent or more. The conversion of monomer to polymer may be about 100 weight percent or less.

Figure 2:
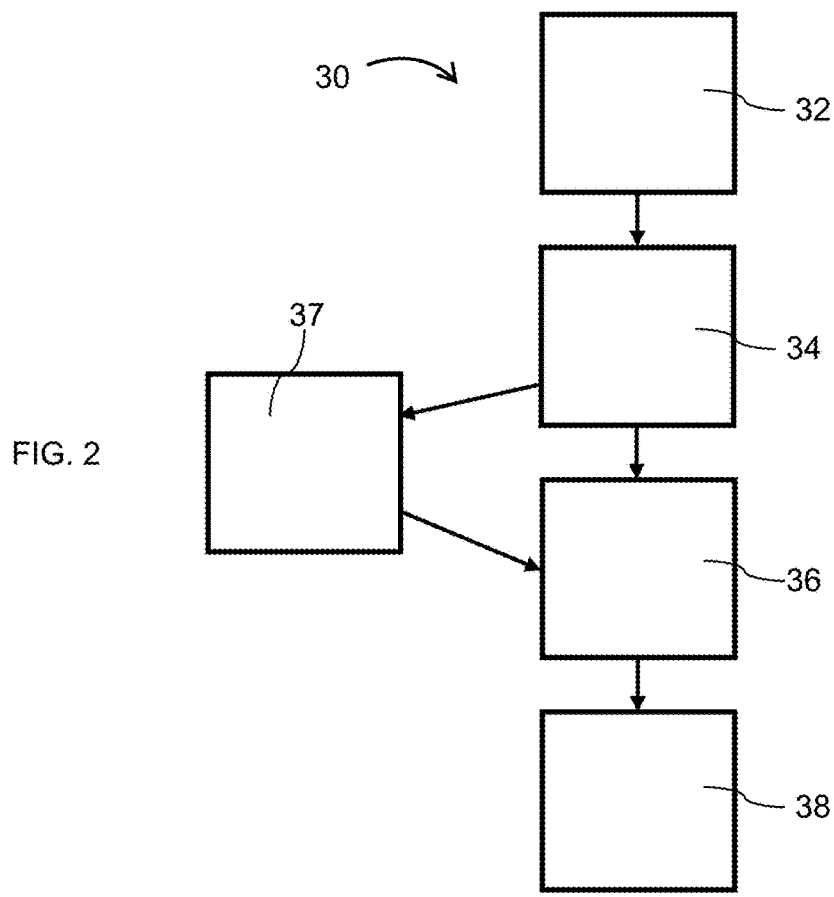
FIG. 2 is a diagram illustrating features of a process for polymerizating a polymer including a 1,1-disubstituted alkene monomer using anionic polymerization.

With reference to FIG. 2, the emulsion polymerization process 30 typically includes a step of developing a multi-phase emulsion system 32. For example, the process may include a step of combining a carrier liquid, a surfactant, and a monomer. It will be appreciated that the components of the emulsion may be added at one time, may be added at different times, or some components may be combined separately. The development of the multi-phase emulsion system 32 typically requires agitation. Depending on the type and intensity of the agitation (along with other factors such as the relative concentration of the monomer and the surfactant), it may be possible to control the particle size of a dispersed phase in the multi-phase emulsion system 32. The process typically includes a step of initiating the polymerization reaction 34. The initiation step preferably occurs after micelles including the monomer have been established. As such, the process may include a step of an activator migrating from the carrier liquid (continuous phase) and into a micelle (e.g., by passing through the surfactant layer). It will be appreciated that an activator may be added into the system prior to the addition of monomer, at the same time as the addition of the monomer, or after addition of a first portion of the monomer and prior to the addition of a second portion of the monomer. After activation of the monomer, the process includes a step of propagating the polymer by an anionic polymerization reaction 36. The propagating step may continue until all of the monomer is consumed, or until the propagation reaction is stopped, such as by quenching 38 or the conditions are altered so that further anionic polymerization reaction stops. The propagation step may also stop by a phase separation of the polymer from the monomer (e.g., where the monomer has difficulty in contacting the reactive end of the polymer molecule). Prior to a step of quenching, there may be one or more additional steps of feed monomer (which may be the same or different from the initial monomer feed), and one or more additional steps of propagating the polymerization reaction. With each such propagating step, the polymer molecular weight generally increases, unless conditions for addition chain activation are provided (for example by adding additional activator). It will be appreciated that the resulting polymer may be capable of further reaction with monomer and may thus be a "living" polymer.

Figure 3A:
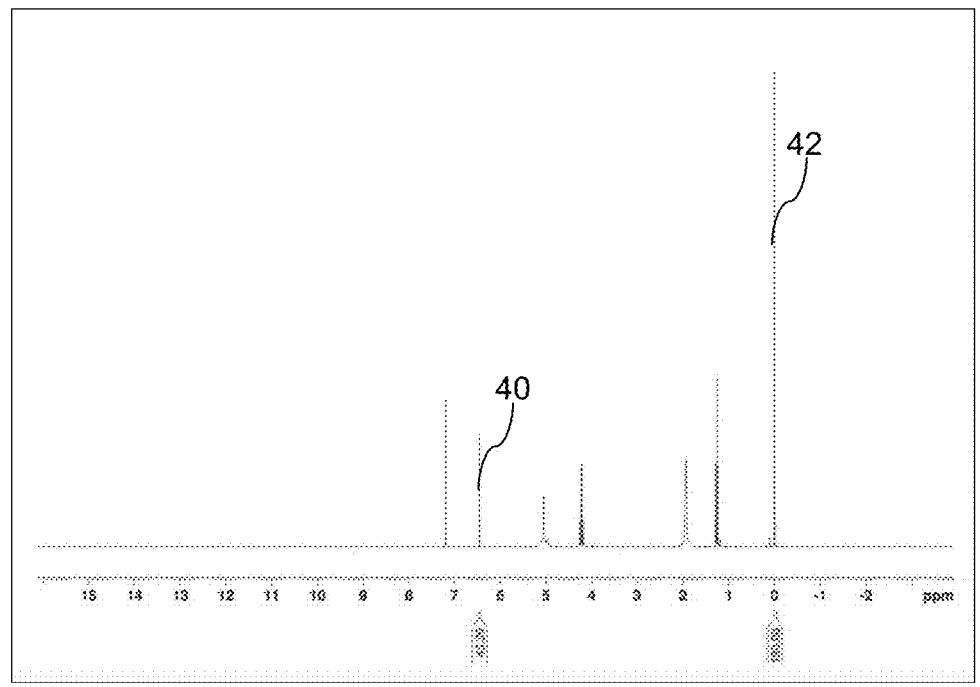
FIGS. 3A and 3B depict representative NMR spectrograms illustrating the conversion of monomer to polymer via emulsion polymerization.
Figure 3B:
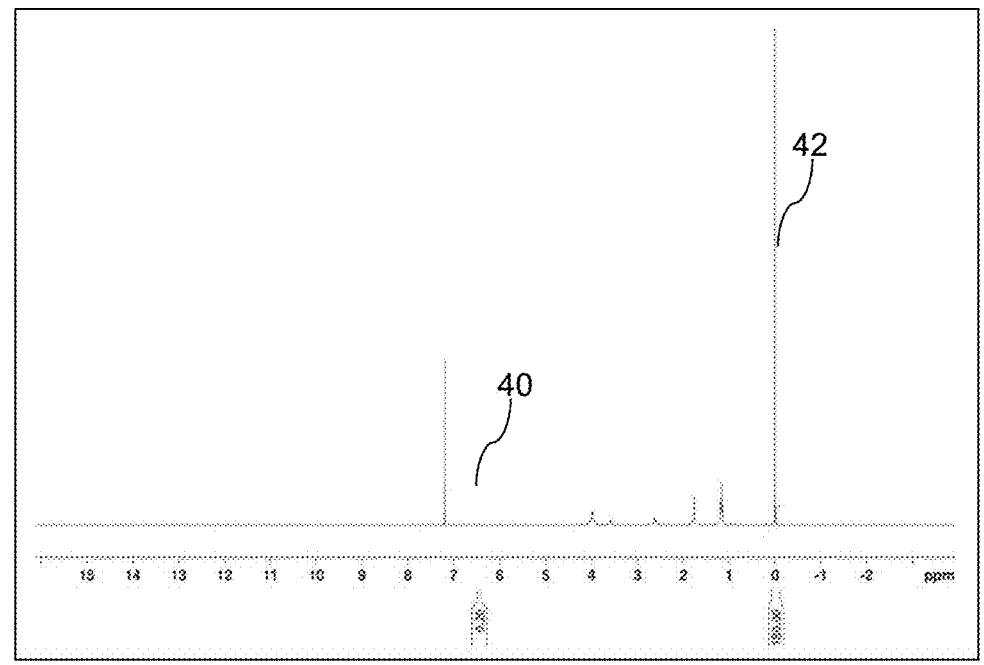

The conversion of monomer to polymer may be measured using NMR spectroscopy, such as illustrated in FIG. 3A and FIG. 3B, corresponding to an early and a later stage of a propagation reaction for polymerizing a 1,1-disubstituted alkene monomer. Here, the monomer is diethyl methylene malonate and the concentration of the monomer can be monitored by the peak at about 6.45 ppm 40 corresponding to the reactive double bond of the monomer. Hexamethyldisiloxane is used here an internal standard (i.e., internal reference) 42 and is seen at about 0 ppm. It will be appreciated that other compounds may be employed as an internal standard. In FIG. 3A, the NMR spectrogram was measured on a first aliquot taken from a specimen initiated with sodium benzoate at a molar ratio of monomer to initiator of about 100:1. The first aliquot was taken after the reaction had propagated for about 30 seconds at room temperature. The first aliquot was quenched with an acid to stop the propagation reaction. FIG. 3B shows the NMR spectrogram from a second aliquot taken from the same specimen after about 5 minutes of the propagation reaction. As seen in FIG. 3B, the monomer is no longer detectable as evidenced by a lack of the reactive double bond peak at about 6.45 ppm 40.

The polymers according to the teachings herein preferably have a number average molecular weight or a weight average molecular weight that is about 700 g/mole or more, more preferably about 2,000 g/mole or more, even more preferably about 10,000 g/mole or more, and most preferably about 20,000 g/mole or more. The molecular weight of the polymer may be sufficiently low so that the polymer may be easily processed. The number average molecular weight or the weight average molecular weight preferably is about 3,000,000 g/mole or less, more preferably about 1,000,000 g/mole or less, even more preferably about 500,000 g/mole or less, and most preferably about 200,000 g/mole or less.

The resulting polymer may be a relatively low molecular weight polymer having a number average molecular weight of about 40,000 g/mole or less, about 30,000 g/mole or less, or about 20,000 g/mole or less. The resulting polymer may be a relatively high molecular weight polymer having a number average molecular weight of greater than 40,000 g/mole, about 60,000 g/mole or more, or about 100,000 g/mole or more.

The resulting polymer may be characterized by a polydispersity index of about 1.00 or more or about 1.05 or more. The resulting polymer may be characterized by a polydispersity index of about 10 or less, preferably about 7 or less, more preferably about 4 or less, and most preferably about 2.3 or less. The resulting polymer may have a narrow molecular weight distribution such that the polydispersity index is about 1.9 or less, about 1.7 or less, about 1.5 or less, or about 1.3 or less.

Surprisingly, by employing an acid containing compound according to the teachings herein, it may be possible to reduce the polydispersity of a polymer (e.g., of a block polymer block) without a substantive reduction in the polymerization reaction rate. For example, the polydispersity of the ratio of the polymer prepared with the acid containing compound to the polydispersity of a polymer prepared using the same method except without the use of the acid containing compound may be about 0.9 or less, about 0.8 or less, about 0.7 or less, or about 0.6 or less. The ratio of the time for converting 80% of the monomer to polymer for the process including the acid containing compound to the time for converting 80% of the monomer to polymer in the identical process (except without the acid containing compound) preferably is about 5 or less, more preferably about 3 or less, even more preferably about 2 or less, and most preferably about 1.5 or less.

Figure 4:
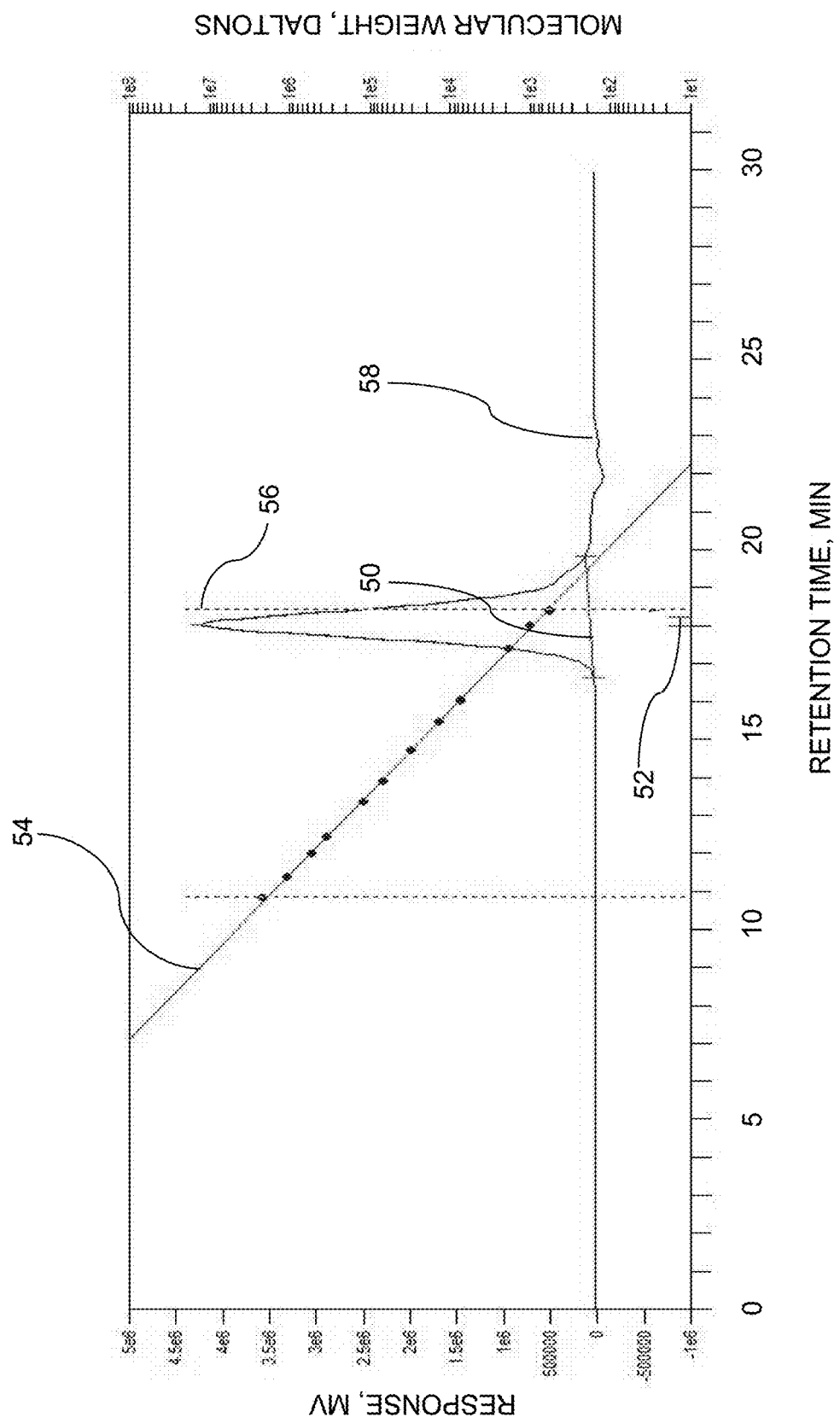
FIG. 4 is a representative GPC chromatogram employed for the characterization of the molecular weight distribution of a polymer according to the teachings herein.

The molecular weight of the polymer may be measured using gel permeation chromatography (i.e., GPC). FIG. 4, illustrates a GPC curve for a homopolymer prepared by polymerizing diethyl methylene malonate in an emulsion system with deionized water as the carrier liquid. Sodium benzoate is used as the activator for the anionic polymerization of the monomer. The molar ratio of monomer to the sodium benzoate activator is about 100:1. The reaction was continued until about 100 percent of the monomer was converted to polymer. The GPC curve 58 of the resulting homopolymer is shown in FIG. 4. This sample has a single peak which defines an area 50 for calculating the molecular weight characteristics of the polymer (e.g., weight average molecular weight, peak molecular weight, number average molecular weight, z-average molecular weight, and polydispersity index). The GPC curve 58 shows the signal intensity (which correlates with concentration) as a function of the retention time in minutes. The calibration curve 54 is also shown in FIG. 4. The calibration curve shows the retention time for a series of PMMA standards of known molecular weight. The low limit 56 for measuring the molecular weight based on these standards is about 200 daltons. The polymer of diethyl methylene malonate characterized in FIG. 4 has a number average molecular weight of about 747, a weight average molecular weight of about 943, and a polydispersity index (i.e., Mw/Mn) of about 1.26.

The emulsion micelle or polymer particle size and/or particle size distribution (e.g., after the completion of polymerization) may be controlled based on process considerations, based on product control considerations, based on application requirements, or any combination thereof. For example, there may be a need for emulsion particles having a unimodal particle size distribution, a multi-modal particle size distribution (e.g., a bimodal distribution), a narrow particle size distribution, a broad particle size distribution, or any combination thereof. In some situations, it may be desirable to prepare generally large emulsion particles (i.e., having a number average radius of about 1 μm or more or a number average diameter of about 2 μm or more, preferably having a number average radius of about 2 μm or more). In other situations, it may be desirable to prepare generally small emulsion particles (i.e., having an average radius of less than about 1 μm, preferably about 0.7 μm or less). The emulsion particles preferably have a number average diameter of about 10 mm or less, about 2 mm or less, about 1 mm or less, about 300 μm or less, about 100 μm or less, or about 50 μm or less. The emulsion particles preferably have a number average diameter of about 0.01 μm or more, about 0.02 μm or more, about 0.05 μm or more, about 0.10 μm or more.

Control of the particle size may be accomplished by any known means. For example, the particle size may be controlled by the amount and/or type of surfactant, the type of any agitation, the amount of agitation, or any combination thereof. By way of example, mechanical agitation, by stirring or otherwise, may be varied (e.g., by varying the mixing speed) to obtain a desired particle size. In general, the particle size may decrease with increasing mixing speed. However, as the mixing speed increases, a plateau may be reached where further increases in mixing speed does not affect the particle size. In general, it may be possible to obtain smaller particle size (e.g., generally small emulsion particle size) using other means of agitation, such as sonication. When using sonication, the frequency preferably is about 0.2 kHz or more, more preferably about 1 kHz or more, even more preferably about 5 kHz or more, and most preferably about 20 kHz or more. Typically the frequency is about 1000 kHz or less, about 500 kHz or less, about 200 kHz or less, or about 100 kHz or less.

It will be appreciated that particle size may be also controlled after the completion of polymerization. For example, two or more emulsions having different number average particle size and/or different particle size distributions may be combined to achieve a desired resulting number average particle size and/or a desired resulting particle size distribution. As used herein, the particle size distribution may be characterized by any known method. For example, the particle size distribution may be characterized by the standard deviation of the particle size, the modality (i.e., number of peaks) of a particle size distribution curve, or a ratio of the average particle size to the number average particle size. The ratio of the standard deviation of the particle size to the number average particle size preferably is about 0.80 or less, more preferably about 0.60 or less, even more preferably about 0.45 or less, and most preferably about 0.30 or less.

The emulsion polymer according to the teachings herein may be characterized as an elastomer. For example, the emulsion polymer may be substantially free of a melting temperature and substantially free of a glass transition temperature of about 15° C. or more.

The emulsion polymer according to the teaching herein may be characterized as a thermoplastic having a melting temperature and/or a glass transition temperature of about 15° C. or more, about 50° C. or more, about 80° C. or more, about 100° C. or more, or about 120° C. or more. Polymers having a high glass transition temperature include those having hydrocarbonyl groups that provide steric hindrance that reduce the mobility of polymer molecules in the melt state. The melting temperature and/or the glass transition temperature of the thermoplastic may be about 250° C. or less, about 200° C. or less, or about 150° C. or less.

The emulsion polymer according to the teachings herein may be characterized as a block copolymer including at least one block having a glass transition temperature or melting temperature of about 15° C. or more (e.g., about 50° C. or more, about 80° C. or more, or about 100° C. or more) and at least one different block having no melting temperature above 15° C. and having a glass transition temperature of less than 15° C. (e.g., about 10° C. or less, about 0° C. or less, or about −20° C. or less). In one aspect, a block copolymer may be prepared with blocks that are not miscible so that the resulting block copolymer has multiple phases at room temperature. As such, the block copolymer may have a first glass transition temperature corresponding to the first polymer block and a second glass transition temperature corresponding to the second polymer block. It will be appreciated that the glass transition temperature of the blocks may be tailored based on the monomer or monomers used in the particular block and/or based on end effects (which includes the effect of the number of monomer units in the block). For purposes of illustration, a polymer block consisting essentially of, or consisting entirely of: (1) diethyl methylene malonate homopolymer is expected to have a glass transition temperature of about 25° C. to about 45° C. (preferably about 35° C.), (2) fenchyl methyl methylene malonate is expected to have a glass transition temperature of about 125° C. to about 155° C. (preferably about 143° C.), (3) methyl methoxyethyl methylene malonate is expected to have a glass transition temperature of about −15° C. to about +10° C. (preferably about 0° C.), (4) hexyl methyl methylene malonate is expected to have a glass transition temperature of about −45° C. to about −20° C. (preferably about −34° C.), (5) dibutyl methylene malonate is expected to have a glass transition temperature of about −55° C. to about −35° C. (preferably about −44° C.). It may be possible to prepare a block copolymer having multiple glass transition temperatures, such as a first glass transition temperature characteristic of a first polymer block and a second glass transition temperature characteristic of a second polymer block. In some block copolymers, a single glass transition is observed indicating that a single phase is formed, indicating that the two polymer blocks have substantially the same glass transition temperature (e.g., a difference of about 20° C. or less, about 10° C. or less, or both).

The emulsion polymer according to the teachings herein may be a characterized as a random copolymer and/or having a polymer block that is a random copolymer. The random copolymer may include a primary monomer (e.g., present at a concentration of about 50 mole percent or more) and a secondary monomer randomly distributed through the polymer chain and having a concentration of less than 50 mole percent. The properties of the random copolymer will generally differ from the properties of a homopolymer consisting entirely of the primary monomer. For example, as the amount of the secondary monomer is increased from about 0.5 mole percent to about 49.5 mole percent, the glass transition temperature of the random copolymer may shift from a glass transition temperature characteristic of the primary monomer towards a glass transition temperature characteristic of the secondary monomer. When prepared as a random copolymer, the polymer typically has a single glass transition temperature (e.g., even when a mixture of a homopolymer of the primary monomer and a homopolymer of the secondary monomer, at the same concentration, exhibits multiple glass transition temperatures).

The homopolymer of the primary monomer may be a semicrystalline polymer. Typically, when a secondary monomer is added in preparing a random copolymer, the secondary monomer will partially inhibit the ability of the primary monomer to crystallize, resulting in a random copolymer having different properties from the homopolymer such as a lower crystallinity, a lower flexural modulus, a lower melting temperature, or any combination thereof. For example, the selection of the secondary monomer and/or the amount of the secondary monomer in the random copolymer may be selected so that the random copolymer has a melting temperature that is reduced (i.e., relative to the homopolymer of the primary monomer) by about 5° C. or more, by about 10° C. or more, by about 15° C. or more, or by about 20° C. or more. The selection of the secondary monomer and/or the amount of the secondary monomer in the random copolymer may be selected so that the random copolymer has a crystallintity that is reduced (i.e., relative to the homopolymer of the primary monomer) by about 10% or more, by about 20% or more, by about 40% or more, or by about 60% or more.

The resulting polymer may be a block copolymer including at least a first polymer block and a second polymer block different from the first polymer block. The first polymer block and the second polymer block may differ with respect to one or any combination of the following properties: peak melting temperature, final melting temperature, crystallinity, glass transition temperature, flexural modulus, tensile modulus, elongation at failure, gas barrier properties, or adhesion properties. For example, the first polymer block and the second polymer block may have melting temperatures (peak melting temperatures and/or final melting temperatures) differing by about 10° C. or more, about 20° C. or more, about 30° C. or more, or about 50° C. or more. It will be appreciated that one polymer block may have a melting temperature and the other polymer block may be free of crystalline polymer so that there is no measurable melting temperature. The first polymer block and the second polymer block may have glass transition temperatures differing by about 10° C. or more, about 20° C. or more, about 30° C. or more, or about 40° C. or more. The first polymer block and the second polymer block may have crystallinities that differ by about 10% or more, about 15% or more, about 20% or more, about 25% or more, or about 30% or more. The first polymer block and the second polymer block may have moduli (e.g., flex modulus, tensile modulus, or both) having a ratio of about 1.5 or more, about 2 or more, about 4 or more, about 8 or more, or about 15 or more. The first polymer block and the second polymer block may have a ratio of elongation at failure and/or a ratio of tensile strength of about 2 or more, about 3 or more, about 4 or more, or about 6 or more.

The degree of blockiness (i.e, the blockiness index, or BI) in a random copolymer may be calculated by the ratio of the concentration of diad fractions of a first monomer (e.g., a primary monomer that is a 1,1-disubstituted alkene compound) added to the second monomer f(M1−M2) plus the diad fractions of the second monomer added to the first monomer f(M2−M1) to the theoretical concentration of diad fractions for a statistical random copolymer $2 X_{M1} (1-X_{M1})$, where $X_{M1}$ is the molar fraction of first monomer:

$$BI=(f(M1-M2)+f(M2-M1))/(2X_{M1}(1-X_{M2}))$$

By definition a true statistically random copolymer has a BI of one (1.0). Blocky random copolymers will have a lower concentration of M1–M2 and M2–M1 diad fractions, and BI will be less than 1.0. Block copolymers will have very low concentrations of M1–M2 and M2–M1 diad fractions and BI will be much less than 1 and approach zero. On the other end, alternating copolymers having $X_{M1} \geq 0.5$ will have $BI = 1 + (1/X_{M1})$. The concentration of the diad fractions and $X_{M1}$ may be measured using $^{13}C$ NMR spectroscopy, using analogous peak assignments and techniques described by Yi-Jun Huange et al. in "Random Copolymers of Propylene Oxide and Ethylene Oxide Prepared by Double Metal Cyanide Complex Catalyst", Chinese Journal of Polymer Science, 20:5, 2002, pages 453-459, incorporated herein by reference in its entirety.

Preferred random copolymers have a BI of about 0.70 or more, more preferably about 0.75 or more, even more preferably about 0.80 or more, even more preferably about 0.85 or more, even more preferably about 0.90 or more, and most preferably about 0.95 or more. Preferred random copolymers have a BI preferably less than about $1+(0.8/x_{M1})$, more preferably less than about $1+(0.5/x_{M1})$, even more preferably less than about $1+(0.25/x_{M1})$, and most preferably less than about $1+(0.10/x_{M1})$ where $x_{M1}$ is the molar fraction of primary monomer in the copolymer and $x_{M1}$ is at least 0.5.

The resulting emulsion polymer may be employed in a polymeric composition including one or more additives, such as antioxidants, heat stabilizers, light stabilizers, process stabilizers, lubricants, antiblocking agents, antistatic agent, anti-fogging agents, solvents, plasticizers, fillers, antistatic agents, coupling agents (e.g., for the fillers), cross-linking agents, nucleating agent, anti-blocking agent, defoaming agents, pigments, colorant, flame retardant additives, flow aid, lubricant, slip agent and other processing aids known to the polymer compounding art. Suitable flame retardants may include halogen containing flame retardants and halogen free flame retardants.

Polymeric compositions may comprise one or more other fillers, such as a filler particle (e.g., fibers, powders, beads, flakes, granules, and the like). The filler particle may be a fiber (e.g., having an aspect ratio of the longest direction to each perpendicular direction that is greater than 10). The filler particle may be a particle that is not a fiber (e.g., having an aspect ratio of the longest direction to a perpendicular direction that is less than 10, less than 8, or less than 5). The filler may be formed of an organic material and/or an inorganic material. Examples of organic fillers include fillers derived from biomass and fillers derived from polymers. Inorganic fillers include, nonmetallic materials, metallic materials, and semiconductor material. For example, the filler particle may include alumina silicate, aluminum hydroxide, alumina, silicon oxide, barium sulfate, bentonite, boron nitride, calcium carbonate (e.g., activated calcium carbonate, light calcium carbonate, or heavy calcium carbonate), calcium hydroxide, calcium silicate, calcium sulfate, carbon black, clay, cotton flock, cork powder, diatomaceous earth, dolomite, ebonite powder, glass, graphite, hydrotalcite, iron oxide, iron metallic particles, kaolin, mica, magnesium carbonate, magnesium hydroxide, magnesium oxide, phosphide, pumice, pyrophyllite, sericite, silica, silicon carbide, talc, titanium oxide, wollastonite, zeolite, zirconium oxide, or any combination thereof. The filler particles may be present at a concentration of about 0.1 weight percent or more, about 1 weight percent or more, about 5 weight percent or more, or about 10 weigh percent or more. The filler particles may be present at a concentration of about 70 weight percent or less, about 50 weight percent or less, about 35 weight percent or less, or about 25 weigh percent or less. The filler particles preferably have one, two, or three dimensions that are about 1 mm or less, about 0.3 mm or less, about 0.1 mm, about 50 µm or less, about 10 µm or less. The filler particles preferably have one, two, or three dimensions that are about 0.1 µm or more, about 0.3 µm or more, or about 1 µm or more.

The polymeric compositions according to the teachings herein may include a plasticizer for adjusting the properties of the final polymer for the desired use. The plasticizer may be added prior to, during, or after polymerization. For example, in certain embodiments, a suitable plasticizer can be included with the 1,1-disubstituted alkene monomer. Generally, suitable plasticizers can include plasticizers used to modify the rheological properties of adhesive systems including, for example, straight and branched chain alkylphthalates such as diisononyl phthalate, dioctyl phthalate, and dibutyl phthalate, as well as partially hydrogenated terpene, trioctyl phosphate, epoxy plasticizers, toluene-sulfamide, chloroparaffins, adipic acid esters, sebacates such as dimethyl sebacate, castor oil, xylene, 1-methyl-2-pyrrolidione and toluene. Commercial plasticizers such as HB-40 manufactured by Solutia Inc. (St. Louis, Mo.) can also be suitable.

The process may include one or more steps of monitoring or otherwise measuring the conversion rate of the monomer to polymer. The concentration of the remaining monomer may be determined for example using NMR spectroscopy. For example, quantitative NMR spectroscopy may be employed to measure the concentration of alkylene groups (e.g., 1-ethylene groups) remaining in the emulsion system.

The emulsion polymer of the current teaching may be mixed with one or more additional polymers for preparing a polymeric composition. The concentration of the emulsion polymer in the polymeric composition may be about 1 weight percent or more, about 5 weight percent or more, about 10 weight percent or more, about 20 weight percent or more, or about 50 weight percent or more, based on the total weight of the polymers in the polymeric composition. The emulsion polymer may be present in the polymeric composition at a concentration of about 100 weight percent or less, about 95 weight percent or less, or about 90 weight percent or less, or about 60 weight percent or less, based on the total weight of the polymers in the polymeric composition.

The process may include one or more steps of removing some or all of the carrier liquid from the emulsion polymer. The process of removing the carrier liquid may use heat, reduced pressure or both for separating the polymer from the carrier liquid. The process of removing the carrier liquid may include a step of filtering and/or a step of adding one or more additional liquids to the emulsion.

The process may include one or more steps of terminating (i.e., quenching) the anionic polymerization reaction. For example, polymerization can be quenched by contacting the emulsion with an anionic polymerization terminator. In some embodiments the anionic polymerization terminator is an acid. In some embodiments it is desirable to utilize a sufficient amount of the acid to render the polymerization mixture (e.g., the emulsion) slightly acidic, preferably having a pH of less than 7, more preferably less than 6. Exemplary anionic polymerization terminators include, for example, mineral acids such as methanesulfonic acid, sulfuric acid, and phosphoric acid and carboxylic acids such as acetic acid and trifluoroacetic acid.

The polymers and polymer compositions according to the teachings herein (e.g., after removing some or all of the carrier liquid) may have one or more rheological properties (e.g., melt index, melt flow rate, viscosity, melt strength, and the like) suitable for processing the polymer with known polymer processing equipment. For example, the polymer or polymer composition including 1,1-disubstituted alkene compounds may be processed using extrusion, co-extrusion, injection molding, insert molding, co-injection molding, calendaring (e.g., using two or more rolls), blow molding, compression molding, thermoforming, rolling, spray coating. For example, the polymeric material (i.e., the polymer or the polymer composition) may be fed through a processing apparatus having a screw and a barrel assembly wherein the polymeric material is conveyed along the screw at a temperature at which the polymeric material is at least partially in a liquid state (e.g., above any glass transition temperature and above any melting temperature).

The polymers according to the teachings herein preferably adhere to one or more of the following substrates: aluminum, steel, glass, silicon, or wood. For example, when separating two substrates having the polymer placed between the substrates, the separation of the substrates may result in cohesive failure of the polymer, where some polymer remains on the surfaces of the substrates.

The polymers according to the teachings herein may be employed in extruded, blow molded, injection molded, thermoformed, or compression molded articles. The polymers may be employed as an adhesive. For example, the polymers may be employed in a pressure sensitive adhesive composition. The polymers may be employed as a coating, such as a protective coating. The polymer may be employed as a primer layer over a substrate.

Melting temperatures and glass transition temperatures are measured using differential scanning calorimetry on a sample of about 0.5-1.0 mg. The sample is heated at a rate of about 10° C./min and then cooled at a rate of about 20° C./min.

The molecular weight is determined using gel permeation chromatography. GPC samples are prepared by first quenching with trifluoroacetic acid and then drying the polymer to remove the carrier liquid (e.g., the water). The dried polymer is dissolved in tetrahydrofuran (THF). About 25 uL of the dissolved polymer solution is injected into the THF eluent having a flow rate of 1 mL/min. Two columns with 5 micron, highly crosslinked polystyrene/divinylbenzene matrix particles are employed. These columns are designed to measure molecular weights of linear polymers from 200 to 2,000,000. The column pressure is about 65 bar and the column temperature is about 35° C. The elution time is 30 minutes. The column is calibrated using PMMA standards. As such, the units for molecular weight are relative based on the standard PMMA equivalent molecular weights.

Monomer conversion is calculated using quantitative NMR. A 300 MHz NMR is employed. Any residual polymerization reaction of the emulsion polymerization specimen is quenched prior to NMR analysis by adding trifluoroacetic acid. The preferred solvent is DMSO-d6 as it is a polar aprotic solvent. When the solvent is added to the emulsion, the aqueous and non-aqueous phases become miscible. Acetic acid is added as an internal standard and is suitable for these monomer compositions. The double bond intensity at about 6.45 ppm is measured to determine the concentration of unconverted monomer. This double bond is a singlet for symmetrical monomers such as diethyl methylene malonate and dibutyl methylene malonate, and it is a doublet for asymmetrical monomers such as hexyl methyl methylene malonate. Four NMR scans are run on each specimen with a 20 second delay between scans.

EXAMPLES

Example 1 is a polymer prepared by emulsion polymerization of diethyl methylene malonate at a temperature of about 23° C. A 100 ml PYREX® beaker is charged with about 20.955 g of deionized water and 0.045 g of a surfactant, 4-dodecylbenzenesulfonic acid (DBSA). The water and surfactant are mixed for about 10 minutes at 500 rpm. About 1 mL of a 1 weight percent sodium benzoate solution in deionized water is added to the mixture and mixing is continued for about 5 minutes. About 9 g of diethyl methylene malonate is then added dropwise while mixing at about 1500 rpm. The sodium benzoate acts as an activator for the polymerization. The molar ratio of monomer to activator is about 500:1. The polymerization method is anionic in nature and occurs in the monomer micelles dispersed in the deionized water. The final ratio of water to monomer/polymer is about 70:30. The reaction is monitored using quantitative NMR by removing an aliquot of the emulsion, quenching with trifluoroacetic acid, mixing with DMSO-d6, and adding acetic acid as the internal standard. After 99.9% or more of the monomer is converted to polymer as determined by the quantitative NMR, about 100 ppm of trifluoroacetic acid is added to quench the reaction. The polymer is then characterized using gel permeation chromatography. The GPC is calibrated using PMMA standards and is used to measure the molecular weight distribution of the polymer. Example 1 has a number average molecular weight of about 15,579, a weight average molecular weight of about 21,010, and a polydispersity index of about 1.36.

Examples 2 and 3 are prepared using the same method as Example 1, except the concentration of the sodium benzoate is changed so that the molar ratio of monomer to activator is about 1000:1 and about 100:1, respectively. The conversion of monomer to polymer is greater than about 99.9 percent.

Examples 4 through 6 are prepared using the same method as Example 1, except the molar ratio of monomer to activator is 100:1 and the activator is 1,1,3,3-tetramethylguanidine, pyridine, and sodium silicate, respectively. The conversion of monomer to polymer is greater than about 99.9 percent.

The molecular weight distributions of Examples 1 through 6 are shown in the Table 1.

TABLE 1

|  | Example 1 | Example 2 | Example 3 | Example 4 | Example 5 | Example 6 |
| --- | --- | --- | --- | --- | --- | --- |
|  | Activator | | | | | |
| Sodium Benzoate | X | X | X |  |  |  |
| 1,1,3,3-Tetramethylguanidine |  |  |  | X |  |  |
| Pyridine |  |  |  |  | X |  |

TABLE 1-continued

|  | Example 1 | Example 2 | Example 3 | Example 4 | Example 5 | Example 6 |
|---|---|---|---|---|---|---|
| Sodium Silicate |  |  |  |  |  | X |
| Ratio of monomer to activator | 500:1 | 1000:1 | 100:1 | 100:1 | 100:1 | 100:1 |
| Polymer Properties | | | | | | |
| Conversion of monomer to polymer | >99.9% | >99.9% | >99.9% | >99.9% | >99.9% | >99.9% |
| Number average molecular weight | 15,579 | 55,031 | 747 | 1,173 | 991 | 1,289 |
| Weight average molecular weight | 21,010 | 71,022 | 943 | 1,582 | 1,334 | 1,724 |
| Polydispersity Index | 1.36 | 1.29 | 1.26 | 1.26 | 1.35 | 1.34 |

Example 7 is prepared by emulsion polymerization of diethyl methylene malonate at a temperature of about 23° C. About 20.7 g of deionized water and a surfactant are mixed in a 100 mL PYREX® beaker for about 10 minutes at about 500 rpm. The surfactant is 2,4,7,9-tetramethyl-5-decyne-4,7-diol ethoxylate (commercially available as SURFYNOL® 485) and the amount of the surfactant is about 0.3 g. About 9 g of the monomer, diethyl methyl malonate, is added rapidly (e.g., in less than about 10 seconds) while mixing at about 500 rpm, forming micelles of the monomer in the water. About 0.503 mL of a 1 weight percent sodium benzoate solution is then added dropwise while mixing at 1500-2000 rpm. The sodium benzoate is the activator for the reaction and the ratio of monomer to activator is about 1000:1. The polymerization reaction is continued for about one hour. The polymerization reaction is quenched by adding about 500 ppm (i.e., about 0.05 weight percent) of trifluoroacetic acid to the emulsion. The conversion of monomer to polymer is greater than 99.9 percent as determined by quantitative NMR.

Example 8 is prepared according to the method of Example 7, except the surfactant is 0.3 g of a tri-block copolymer of poly(ethylene glycol)-block-poly(propylene glycol)-block-(polyethylene glycol).

Example 9 is prepared according to the method of Example 7, except the surfactant is 0.3 g of CARBOWET® 138. This surfactant includes alkyl alcohol, polyethylene glycol, and ethoxylated C9-11 alcohols.

Example 10 is prepared according to the method of Example 7, except the surfactant is 0.3 g of sorbitan monopalmitate. This surfactant is a soft solid at room temperature. The reaction temperature is raised to about 46° C. to improve the dispersion of the surfactant during the polymerization process.

Example 11 is prepared according to the method of Example 7, except the surfactant is 0.3 g of IGEPAL® CO-720. This surfactant includes polyoxyethylene (12) nonylphenyl ether, branched.

Example 12 is prepared according to the method of Example 7, except the surfactant is 0.3 g of poly(ethylene glycol) sorbitol hexaoleate.

In examples 7-12, the conversion of monomer to polymer was about 100 percent.

Examples 13-17 are prepared according to the method of Example 7, except the molar ratio of the monomer to the activator (sodium benzoate) is 100:1, 200:1, 500:1, 8000:1, and 16000:1, respectively. Each of the resulting polymers has a conversion of monomer to polymer of about 100 percent. The molecular weight characterization of Example 7 and 13-17 are listed in Table 2.

TABLE 2

|  | Example 7 | Example 13 | Example 14 | Example 15 | Example 16 | Example 17 |
|---|---|---|---|---|---|---|
| Activator | | | | | | |
| Sodium Benzoate | X | X | X | X | X | X |
| Surfactant | | | | | | |
| SURFYNOL ® 485 | X | X | X | X | X | X |
| Ratio of monomer to activator | 1000:1 | 100:1 | 200:1 | 500:1 | 8000:1 | 16000:1 |
| Polymer Properties | | | | | | |
| Conversion of monomer to polymer | ≈onve | ≈onve | ≈onve | ≈onve | ≈onve | ≈onve |
| Number average molecular weight | 4,161 | 9,442 | 7,290 | 6,939 | 3104 | 1226 |
| Weight average molecular weight | 13,535 | 18,605 | 17,782 | 18,038 | 5411 | 2237 |
| Polydispersity Index | 3.25 | 2.5 | 2.43 | 2.60 | 1.94 | 1.82 |

Freeze/thaw stability is evaluated by first measuring the initial viscosity of the polymer specimen. The polymer specimen is then placed in a chamber at a temperature of about −24° C. for about 17 hours, and then to a room temperature of about 22° C. for about 7 hours. This 24 hour cycle is repeated 5 times. The viscosity of the specimen is measured after being at room temperature for about 7 hours. The specimen is also observed for any signs of settling, gelation, or coagulation which would indicate an instable emulsion system. Conversely, no observed signs of settling, gelation, or coagulation indicates a stable emulsion system.

Example FTSS-1 is a sample of poly (diethyl methylene malonate) (i.e., poly(DEMM)) having a number average molecular weight of about 995 and prepared by emulsion polymerization. The initial viscosity of Example FTSS-1 is about 10-22 cPs. After 5 freeze/thaw cycles, the specimen still has a viscosity of about 10-22 cPs. During the 5 cycles, there is no indication of settling, gelation, or coagulation.

Example FTSS-2 is a sample of poly (dibutyl methylene malonate) (i.e., poly(DBMM)) having a number average molecular weight of about 2121 and prepared by emulsion polymerization. The initial viscosity of Example FTSS-2 is about 13-24 cPs. After 5 freeze/thaw cycles, the specimen still has a viscosity of about 13-24 cPs. During the 5 cycles, there is no indication of settling, gelation, or coagulation.

Example FTSS-3 is a sample of poly (hexyl methyl methylene malonate) (i.e., poly(HMMM)) having a number average molecular weight of about 5018 and prepared by emulsion polymerization. The initial viscosity of Example FTSS-3 is about 15-25 cPs. After 5 freeze/thaw cycles, the specimen still has a viscosity of about 15-25 cPs. During the 5 cycles, there is no indication of settling, gelation, or coagulation.

Example FTSS-4 is a sample of poly(DEMM) having a number average molecular weight of about 25,000 prepared by emulsion polymerization. The polymer is tested for freeze/thaw stability. After 5 freeze/thaw cycles, Example FTSS-4 shows signs of settling, gelation and coagulation, and does not flow.

Examples FTSS-5, FTSS-6, FTSS-7, FTSS-8, and FTSS-9 are samples of poly(DEMM) are prepared having number average molecular weight of 25,345 through 498,003, as shown in Table 3. About 0.05 weight percent of hydroxyethyl cellulose stabilizer is added to each of the polymer samples. After 5 freeze/thaw cycles, there is no evidence of settling, gelation, or coagulation, and the final viscosity is substantially unchanged from the initial viscosity.

polymerization is performed at about 23° C. using a weight ratio of deionized water to monomer/polymer of about 70:30. The surfactant is 2,4,7,9-tetramethyl-5-decyne-4,7-diol ethoxylate (commercially available as SURFYNOL® 485), or 4-dodecylbenzenesulfonic acid (DBSA), or a mixture of the two surfactants. The surfactant and amount of surfactant for each Example is shown in Table 4. The activator is sodium benzoate and is added at a monomer to activator ratio of about 100:1. The monomer is added while mixing the deionized water, surfactant, and activator at about 1500 rpm. The monomer is added in total within about 5 seconds. The approximate times for 95% and 99% conversion of monomer to polymer (as measured using quantitative NMR spectroscopy) is listed in Table 4. The reaction is continued for 4 hours. The final conversion is also listed in Table 4. About 500 ppm of trifluoroacetic acid is added to the emulsion to quench the reaction. The molecular weight of the resulting polymer is then measured using GPC. The weight average molecular weight, number average molecular weight and polydispersity index for each polymer is given in Table 4. Although addition of DBSA slows down the reaction rate, addition of small amounts of DBSA (e.g.,

TABLE 3

|  | Example FTSS-5 | Example FTSS-6 | Example FTSS-7 | Example FTSS-8 | Example FTSS-9 |
|---|---|---|---|---|---|
| Number Average Molecular Weight | 25,345 | 50,989 | 125,129 | 209,039 | 498,003 |
| Initial Viscosity, cPs | 9 to 22 | 10 to 24 | 10 to 20 | 10 to 24 | 15 to 25 |
| Viscosity after 5 freeze/thaw cycles | 11 to 25 | 12 to 24 | 10 to 20 | 12 to 24 | 12 to 23 |
| Settling/Gelation/Coagulation after 5 freeze/thaw cycles | None | None | None | None | None |

Examples E-1, E-2, E-3, E-4, E-5, E-6, E-7, and E-8 are prepared by polymerizing diethyl methyl malonate monomer using different mixtures of surfactants. The emulsion less than about 1500 ppm) results in a high polymerization reaction rates and polymers having a narrow molecular weight distribution.

TABLE 4

|  | Example E-1 | Example E-2 | Example E-3 | Example E-4 | Example E-5 | Example E-6 | Example E-7 | Example E-8 |
|---|---|---|---|---|---|---|---|---|
| Surfynol 485 | 2 wt. % | 2 wt. % | 2 wt. % | 2 wt. % | 2 wt. % | 2 wt. % | 2 wt. % | 0 wt. % |
| DBSA, ppm | 0 | 500 | 1000 | 2000 | 3000 | 4000 | 5000 | 5000 |
| Number average molecular weight | 6939 | 14109 | 2756 | 931 | 721 | 687 | 764 | 15579 |
| Weight average molecular weight | 18038 | 17258 | 4104 | 1150 | 908 | 904 | 950 | 21010 |
| Polydispersity Index | 2.60 | 1.22 | 1.49 | 1.24 | 1.26 | 1.32 | 1.24 | 1.35 |
| Monomer Conversion, % (after 4 hours) | 99.98 | 99.99 | 99.99 | 99.32 | 98.83 | 89.73 | 89.03 | 16.92 |
| Time for 95% conversion (min) | <1 | ≈4 | ≈6 | ≈250 | ≈300 | >480 | >480 | >480 |
| Time for 99% conversion (min) | ≈7 | ≈7 | ≈8 | ≈400 | >480 | >480 | >480 | >480 |

Homopolymer Example H-1 is prepared via emulsion polymerization using diethyl methyl malonate. The emulsion is prepared by adding a surfactant, deionized water, and diethyl methyl malonate monomer to a reaction vessel and stirring the mixture to form an emulsion of the monomer in the water. The polymerization reaction is conducted at about 23° C. The weight ratio of the deionized water to the monomer/polymer is about 70:30. The surfactant is 2,4,7,9-tetramethyl-5-decyne-4,7-diol ethoxylate (commercially available as SURFYNOL® 485) and the amount of the surfactant is about 2 weight percent, based on the total weight of the emulsion. The reaction is initiated by adding sodium benzoate to the reaction vessel. The molar ratio of diethyl methylene malonate monomer to sodium benzoate is about 200:1. The reaction time is about 10 minutes and the conversion of the monomer to polymer is greater than 99.9%. The reaction is quenched by adding about 500 ppm of trifluoroacetic acid to the emulsion. The resulting polymer isolated and then dissolved in a solvent of dichloromethane or tetrahydrofuran. The solution is then precipitated at −25° C. about 4 times the volume of methanol. The precipitate is then further washed with a mixture of hexane and methanol (1:1 ratio by weight) at −25° C. The precipitate is filtered or otherwise separated from the liquids. The washing step removed essentially all of the surfactant and other non-reaction materials or impurities. The recovered polymer has a weight average molecular weight greater than 50,000 and a glass transition temperature of about 35° C.

Homopolymer Example H-2 is prepared using the same procedure as for Example H-1, except the diethyl methyl malonate monomer is replaced with fenchyl methyl methylene malonate monomer and the initiator is sodium silicate at a molar ratio of monomer to activator of about 200:1. The recovered polymer has a weight average molecular weight greater than 50,000 and a glass transition temperature of about 143° C.

Homopolymer Example H-3 is prepared using the same procedure as for Example H-1, except the diethyl methyl malonate monomer is replaced with methylmethoxy ethyl methylene malonate monomer and the initiator is sodium silicate at a molar ratio of monomer to activator of about 200:1. The recovered polymer has a weight average molecular weight greater than 50,000 and a glass transition temperature of about 0° C.

Homopolymer Example H-4 is prepared using the same procedure as for Example H-1, except the diethyl methyl malonate monomer is replaced with hexyl methyl methylene malonate monomer and the initiator is sodium silicate at a molar ratio of monomer to activator of about 200:1. The recovered polymer has a weight average molecular weight greater than 50,000 and a glass transition temperature of about −34° C.

Homopolymer Example H-5 is prepared using the same procedure as for Example H-1, except the diethyl methyl malonate monomer is replaced with dibutyl methylene malonate monomer and the surfactant is sodium silicate at a molar ratio of monomer to activator of about 200:1. The recovered polymer has a weight average molecular weight greater than 50,000 and a glass transition temperature of about −44° C.

Homopolymer Example H-6 is prepared using the same procedure as for Example H-1, except the molar ratio of the diethyl methylene malonate monomer to the sodium benzoate activator is about 100:1. In preparing Example H-6, the solution is agitated using a mixing speed of about 400 rpm. The mixing time is about 1 hour. The resulting emulsion is measured using dynamic light scattering. The polymer particles have a refractive index of about 1.81. The number average particle size is about 28.6 μm with a standard deviation of about 7.6 μm. Homopolymer Example H-7 is prepared using the same procedure as for Example H-6, except the mixing speed was increased to about 1500 rpm. The resulting polymer particles have a refractive index of about 1.81, an average particle size of about 6.44 μm with a standard deviation of about 3.31 μm. Homopolymer Example H-8 is prepared using the same procedure as for Example H-6, except the agitation was achieved using sonication at a frequency of about 40 kHz. The resulting polymer particles have a refractive index of about 1.81, an average particle size of about 0.48 μm with a standard deviation of about 0.09 μm. The homopolymer results for H-1 through H-6 are summarized in Table 5.

TABLE 5

|  | Example H-1 | Example H-2 | Example H-3 | Example H-4 | Example H-5 |
|---|---|---|---|---|---|
| Monomer | DEMM | FMMM | MMOEMM | HMMM | DBMM |
| Type of polymer | homoplymer | homoplymer | homoplymer | homoplymer | homoplymer |
| Weight average molecular weight, Mw | >50,000 | >50,000 | >50,000 | >50,000 | >50,000 |
| Glass Transition Temp., ° C. | 35 | 143 | 0 | −34 | −44 |
| Monomer conversion | >99.9% | >99.9% | >99.9% | >99.9% | >99.9% |

Example M-1 is a mixture of two homopolymers, homopolymer Example H-1 and homopolymer Example H-2 are dissolved together in dichloromethane solvent at a weight ratio of the two homopolymers of 1:1. The polymer mixture is then precipitated from solution by adding methanol (at about −25° C.) at a volume of about 4 times the volume of the solvent. The precipitated polymer is further washed with a 1:1 mixture (by weight) of methanol and hexane (at about −25° C.). The resulting polymer mixture has two glass transition temperatures at about 45° C. and at about 137° C.

Example M-2 is a mixture of two homopolymers, homopolymer Example H-1 and homopolymer Example H-3. The polymer mixture is prepared using the same method as described above for Example M-1, except homopolymer Example H-2 is replaced by homopolymer Example H-3. The resulting polymer mixture has two glass transition temperatures at about 28° C. and at about 12° C.

Example M-3 is a mixture of two homopolymers, homopolymer Example H-1 and homopolymer Example H-4. The polymer mixture is prepared using the same method as described above for Example M-1, except homopolymer Example H-2 is replaced by homopolymer Example H-4. The resulting polymer mixture has two glass transition temperatures at about 25° C. and at about −25° C.

Example M-4 is a mixture of two homopolymers, homopolymer Example H-1 and homopolymer Example H-3. The polymer mixture is prepared using the same method as described above for Example M-1, except homopolymer Example H-2 is replaced by homopolymer Example H-5. The resulting polymer mixture has a single glass transition temperature at about −5° C.

Example M-5 is a mixture of two homopolymers, homopolymer Example H-2 and homopolymer Example H-3. The polymer mixture is prepared using the same method as described above for Example M-1, except homopolymer Example H-1 is replaced by homopolymer Example H-2, and homopolymer Example H-2 is replaced by homopolymer Example H-3. The resulting polymer mixture has two glass transition temperatures at about 131° C. and at about 10° C.

Example M-6 is a mixture of two homopolymers, homopolymer Example H-2 and homopolymer Example H-4. The polymer mixture is prepared using the same method as described above for Example M-1, except homopolymer Example H-1 is replaced by homopolymer Example H-2, and homopolymer Example H-2 is replaced by homopolymer Example H-4. The resulting polymer mixture has two glass transition temperatures at about 132° C. and at about −14° C.

Example M-7 is a mixture of two homopolymers, homopolymer Example H-2 and homopolymer Example H-5. The polymer mixture is prepared using the same method as described above for Example M-1, except homopolymer Example H-1 is replaced by homopolymer Example H-2, and homopolymer Example H-2 is replaced by homopolymer Example H-5. The resulting polymer mixture has two glass transition temperatures at about 129° C. and at about −33° C.

Example M-8 is a mixture of two homopolymers, homopolymer Example H-3 and homopolymer Example H-4. The polymer mixture is prepared using the same method as described above for Example M-1, except homopolymer Example H-1 is replaced by homopolymer Example H-3, and homopolymer Example H-2 is replaced by homopolymer Example H-4. The resulting polymer mixture has two glass transition temperatures at about −7° C. and at about −25° C.

Example M-9 is a mixture of two homopolymers, homopolymer Example H-3 and homopolymer Example H-5. The polymer mixture is prepared using the same method as described above for Example M-1, except homopolymer Example H-1 is replaced by homopolymer Example H-3, and homopolymer Example H-2 is replaced by homopolymer Example H-5. The resulting polymer mixture has two glass transition temperatures at about −9° C. and at about −36° C.

Example M-10 is a mixture of two homopolymers, homopolymer Example H-3 and homopolymer Example H-5. The polymer mixture is prepared using the same method as described above for Example M-1, except homopolymer Example H-1 is replaced by homopolymer Example H-4, and homopolymer Example H-2 is replaced by homopolymer Example H-5. The resulting polymer mixture has a single glass transition temperature at about −37° C.

Examples R-1 through R-10 are random copolymer prepared according to the method of Example H-1 homopolymer, except the monomer of diethyl methyl malonate is replaced with a 1:1 weight ratio of monomer 1 and monomer 2, as listed in Table 5. The resulting polymers are random copolymers having a weight average molecular weight of 50,000 or more, and having a conversion of monomer to polymer of greater than 99.9 weight percent. Each of the random copolymers has a single glass transition temperature as shown in the Table 6.

Example B-1 is a block copolymer prepared by sequentially polymerizing a first polymer block, a second polymer block, and a third polymer block. The first polymer block is prepared as described above for homopolymer Example H-1, except the amount of the monomer is reduced to about one-third of the monomer employed in Example H-1. After preparing the first polymer block, a sample of the polymer (Example B-1 stage 1) is removed, quenched with about 500 ppm of trifluoroacetic acid, precipitated, and washed for analysis, as described above. The remaining polymer is further polymerized by adding a second monomer (fenchyl methyl methylene malonate) to the emulsion to form a second polymer block consisting essentially of the second monomer. The amount of the second monomer is about one-third of the total monomer used in Example H-1. After preparing the second polymer block, a sample of the diblock polymer (Example B-1 stage 2) is removed, quenched with about 500 ppm trifluoroacetic acid, precipitated, and washed for analysis. The remaining polymer is further polymerized by adding an additional amount of the first monomer into the emulsion to polymerize a third polymer block consisting essentially of the first monomer. The amount of the third monomer is about one-third of the monomer employed in Example H-1. The resulting tri-block copolymer (Example B-1 stage 3) is quenched with about 500 ppm of trifluoroacetic acid, precipitated, and washed as described above for hompolymer Example H-1.

TABLE 6

| Example Number | Monomer 1 | Monomer 2 | Glass Transition Temp, ° C. |
|---|---|---|---|
| Example R-1 | Diethyl methylene malonate | fenchyl methyl methylene malonate | 88 |
| Example R-2 | Diethyl methylene malonate | methylmethoxy ethyl methylene malonate | 17 |
| Example R-3 | Diethyl methylene malonate | hexyl methyl methylene malonate | 1 |
| Example R-4 | Diethyl methylene malonate | dibutyl methylene malonate | −4 |
| Example R-5 | fenchyl methyl methylene malonate | methylmethoxy ethyl methylene malonate | 72 |
| Example R-6 | fenchyl methyl methylene malonate | hexyl methyl methylene malonate | 55 |

TABLE 6-continued

| Example Number | Monomer 1 | Monomer 2 | Glass Transition Temp, °C. |
|---|---|---|---|
| Example R-7 | fenchyl methyl methylene malonate | dibutyl methylene malonate | 50 |
| Example R-8 | methylmethoxy ethyl methylene malonate | hexyl methyl methylene malonate | −16 |
| Example R-9 | methylmethoxy ethyl methylene malonate | dibutyl methylene malonate | −22 |
| Example R-10 | hexyl methyl methylene malonate | dibutyl methylene malonate | −38 |

Examples B-2, B-3, and B-4 are block copolymers prepared according to the method described above for Example B-1, except the second monomer of fenchyl methyl methylene malonate is replaced with methylmethoxy ethyl methylene malonate, hexyl methyl methylene malonate, and dibutyl methylene malonate, respectively.

The properties of Examples B-1, B-2, B-3, and B-4 at the end of each of the three stages (single block, diblock, and triblock) are listed in Table 7.

TABLE 7

|  | Example B-1 | Example B-2 | Example B-3 | Example B-4 |
|---|---|---|---|---|
| After stage 1 (single block) | | | | |
| Monomer | DEMM | DEMM | DEMM | DEMM |
| Conversion, wt. % | >99.9 | >99.9 | >99.9 | >99.9 |
| Mn | 16167 | 16191 | 16103 | 16093 |
| Polydispersity Index | 1.3 | 1.3 | 1.3 | 1.3 |
| Glass Transition Temp, °C. | 34 | 35 | 35 | 34 |
| After stage 2 (diblock) | | | | |
| Monomer | FMMM | MMOEMM | HMMM | DBMM |
| Conversion, wt. % | >99.8 | >99.9 | >99.9 | >99.8 |
| Mn | 29384 | 31903 | 30789 | 28263 |
| Polydispersity Index | 2.1 | 1.9 | 1.8 | 2.0 |
| Glass Transition Temp, °C. | 48 and 132 | 8 and 27 | −26 and 23 | −8 |
| After stage 3 (triblock) | | | | |
| Monomer | DEMM | DEMM | DEMM | DEMM |
| Conversion, wt. % | >99.8 | >99.8 | >99.9 | >99.7 |
| Mn | 44102 | 45093 | 44387 | 42561 |
| Polydispersity Index | 2.9 | 2.4 | 2.2 | 2.6 |
| Glass Transition Temp, °C. | 38 and 125 | 15 and 33 | −9 and 32 | 10 |

A pressure sensitive adhesive emulsion composition is prepared by mixing about 67.98 parts deionized water, about 0.03 parts 4-dodecylbenzenesulfonic acid, and about 2.00 parts ethoxylated 2,4,7,9-tetramethyl-5-decyne-4,7-diol at about 700 rpm. A 10% solution of sodium silicate activator in deionized water is added at about 0.42 parts (for a monomer to activator molar ratio of about 200:1) and mixed at about 1,000 rpm. About 27.75 parts hexyl methyl methylene malonate monomer is added in bulk and mixing is continued at about 1,000 rpm. After the polymerization reaction is completed, the emulsion is applied to a steel plate and the water is removed by evaporation. The resulting polymer is a pressure sensitive adhesive and possess representative tack as a result of the polymer. When a crosslinker is added and the PSA material is adhered to steel panel, substantially no polymer is transferred off of the steel panel when a second substrate is applied and removed. The PSA material has good stability after 5 freeze/thaw cycles.

REFERENCE SIGNS FROM DRAWINGS

10 Emulsion system
12 Continuous liquid phase
14 Dispersed phase/Emulsion micelle
16 Surfactant/Surfactant layer
18 Interior of micelle
20 Outer surface of micelle/Outer surface of surfactant layer
22 Inner surface of surfactant layer
24 Interior of micelle
26 Monomer/Polymer
28 Carrier liquid
30 Illustrative steps included in an emulsion polymerization process
32 Step of combining a carrier liquid, surfactant and monomer with agitation to prepare a multi-phase system
34 Step of adding an activator to begin a polymerization reaction
36 Step of propagating the polymer by an anionic polymerization reaction
37 Optional step of adding one or more monomers and/or continuously feeding one or more monomers (e.g., after substantially all of the previously added monomer has been consumed).
38 Optional step of quenching the polymerization reaction
40 About 6.45 ppm on the NMR spectrograph (corresponding to the reactive double bond peak of diethyl methylene malonate)
42 About 0 ppm on the NMR spectrograph-internal reference
50 GPC peak and area of calculation
52 Weight Average Molecular Weight (Mw)

54 Calibration curve (molecular weight v. retention time) based on PMMA standards
56 Lowest molecular weight calibration (200 daltons)
58 GPC Curve

What is claimed is:

1. An emulsion comprising:
   i) 30 weight percent or more of a continuous phase including a carrier fluid including water;
   ii) a dispersed phase including a polymer and having a surfactant layer in contact with the polymer and with the carrier fluid;
   wherein the polymer is present in an amount of about 10 weight percent or more, includes one or more monomers including one or more 1,1-disubstituted alkene compounds, and has a number average molecular weight of about 700 g/mole or more, and wherein the polymer has a polydispersity index of about 1.7 or less.

2. The emulsion of claim 1, wherein the polymer has a number average molecular weight of about 2,000 g/mole to about 1,000,000 g/mole.

3. The emulsion of claim 1, wherein the dispersed phase includes micelles having a number average radius of about 0.10 µm to about 300 µm.

4. The emulsion of claim 3, wherein the concentration of the polymer is about 20 weight percent or more.

5. The emulsion of claim 4, wherein the carrier liquid consists essentially of water, and
   i) the concentration of the carrier liquid is sufficiently high so that the emulsion is capable of flowing; or
   ii) the ratio of the zero shear viscosity of the emulsion to the zero shear viscosity of the polymer at 25° C. is about 0.2 or less.

6. The emulsion of claim 5, wherein the carrier liquid is present in an amount of about 65 weight percent or less, based on the total weight of the emulsion.

7. The emulsion of claim 6, wherein the polymer is formed by a polymerization activated by one or more monomer activators including an ionic metal amide, an hydroxide, a cyanide, a phosphine, an alkoxide, an amine, an organometallic compound, or a metal benzoate; wherein the molar ratio of the one or more monomers to the monomer activators is greater than about 50:1.

8. The emulsion of claim 6, wherein the one or more 1,1-disubstituted alkenes includes methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-n-propyl methylene malonate, ethyl hexyl methylene malonate, methyl fenchyl methylene malonate, ethyl fenchyl methylene malonate, 2-phenylpropyl ethyl methylene malonate, 3-phenylpropyl ethyl methylene malonate, or dimethoxy ethyl methylene malonate.

9. The emulsion of claim 8, wherein the polymer includes a first 1,1-disubstituted alkene and a second 1,1-disubstituted alkene.

10. An emulsion comprising:
    i) 30 weight percent or more of a continuous phase including a carrier fluid including water, wherein the carrier liquid is present in an amount of about 65 weight percent or less, based on the total weight of the emulsion; and
    ii) a dispersed phase including a polymer and having a surfactant layer in contact with the polymer and with the carrier fluid, wherein the dispersed phase includes micelles having a number average radius of about 0.10 µm to about 300 µm and wherein the concentration of the polymer is about 20 weight percent or more;
    wherein the polymer is present in an amount of about 10 weight percent or more, includes one or more monomers including one or more 1,1-disubstituted alkene compounds, and has a number average molecular weight of about 700 g/mole or more;
    wherein the one or more 1,1-disubstituted alkenes includes methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-n-propyl methylene malonate, ethyl hexyl methylene malonate, methyl fenchyl methylene malonate, ethyl fenchyl methylene malonate, 2-phenylpropyl ethyl methylene malonate, 3-phenylpropyl ethyl methylene malonate, or dimethoxy ethyl methylene malonate wherein the polymer includes a first polymer block including about 10 weight percent or more of a first 1,1-disubstituted alkene; and a second polymer block including less than 10 weight percent of the first 1,1-disubstituted alkene.

11. The emulsion of claim 9, wherein the polymer is a random copolymer including the 1,1-disubstituted alkene and a second monomer.

12. The emulsion of claim 6, wherein the one or more monomers includes:
    i) a first 1,1-disubstituted alkene including methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-n-propyl methylene malonate, ethyl hexyl methylene malonate, methyl fenchyl methylene malonate, ethyl fenchyl methylene malonate, 2-phenylpropyl ethyl methylene malonate, 3-phenylpropyl ethyl methylene malonate, or dimethoxy ethyl methylene malonate; and
    ii) a different 1,1-disubstituted alkene including methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-N-propyl methylene malonate, ethyl hexyl methylene malonate, methyl fenchyl methylene malonate, ethyl fenchyl methylene malonate, 2 phenylpropyl ethyl methylene malonate, 3 phenylpropyl ethyl methylene malonate, or dimethoxy ethyl methylene malonate.

13. An emulsion comprising:
i) 30 weight percent or more of a continuous phase including a carrier fluid including water;
ii) a dispersed phase including a polymer and having a surfactant layer in contact with the polymer and with the carrier fluid;
wherein the polymer is present in an amount of about 10 weight percent or more, includes one or more monomers including one or more 1,1-disubstituted alkene compounds, and has a number average molecular weight of about 700 g/mole or more and, wherein the polymer includes a first polymer block including about 10 weight percent or more of a first 1,1-disubstituted alkene; and a second polymer block including less than 10 weight percent of the first 1,1-disubstituted alkene.

14. An emulsion comprising:
i) 30 weight percent or more of a continuous phase including a carrier fluid including water;
ii) a dispersed phase including a polymer and having a surfactant layer in contact with the polymer and with the carrier fluid;
wherein the polymer is present in an amount of about 10 weight percent or more, includes one or more monomers including one or more 1,1-disubstituted alkene compounds, and has a number average molecular weight of about 700 g/mole or more, and wherein the polymer is a block copolymer including a first block having a glass transition temperature of 15° C. or more, and a second polymer block having a glass transition temperature of less than 15° C.

15. The emulsion of claim 1, wherein the 1,1-disubstituted alkene is a compound having a hydrocarbyl group bonded to each of the two carbonyl groups through a direct bond or through an oxygen atom, wherein the 1,1-disubstituted alkene compound has the general formula:

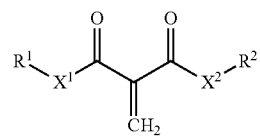

where $X^1$ is a direct bond or an oxygen atom;
$X^2$ is a direct bond or an oxygen atom; and
$R^1$ and $R^2$ are each hydrocarbyl groups.

16. The emulsion of claim 15, wherein the polymer is a random copolymer including the 1,1-disubstituted alkene and a second monomer.

17. The process of claim 15, wherein the polymer is a block copolymer including a first block having a first glass transition temperature and a second block having a second glass transition temperature, wherein the first and second glass transition temperatures differ by about 20° C. or more.

18. An adhesive including the emulsion of claim 1, wherein the adhesive is a water-based adhesive and the carrier liquid consists essentially of water.

19. The adhesive of claim 18, wherein the adhesive is a pressure sensitive adhesive.

20. A coating including the emulsion of claim 1, wherein the coating is a water-based coating and the carrier liquid consists essentially of water.

* * * * *